(12) United States Patent
Gernand et al.

(10) Patent No.: US 11,244,450 B2
(45) Date of Patent: Feb. 8, 2022

(54) SYSTEMS AND METHODS UTILIZING ARTIFICIAL INTELLIGENCE FOR PLACENTAL ASSESSMENT AND EXAMINATION

(71) Applicant: THE PENN STATE RESEARCH FOUNDATION, University Park, PA (US)

(72) Inventors: Alison Gernand, State College, PA (US); James Z. Wang, State College, PA (US); Jeffery Goldstein, Chicago, IL (US); William Parks, Toronto (CA); Yukun Chen, State College, PA (US); Zhuomin Zhang, State College, PA (US); Dolzodmaa Davaasuren, State College, PA (US); Chenyan Wu, State College, PA (US)

(73) Assignees: The Penn State Research Foundation, University Park, PA (US); Northwestern University, Evanston, IL (US); Sinai Health System, Toronto (CA)

( * ) Notice: Subject to any disclaimer, the term of this patent is extended or adjusted under 35 U.S.C. 154(b) by 0 days.

(21) Appl. No.: 16/996,342

(22) Filed: Aug. 18, 2020

(65) Prior Publication Data
US 2021/0056691 A1   Feb. 25, 2021

Related U.S. Application Data

(60) Provisional application No. 62/888,838, filed on Aug. 19, 2019.

(51) Int. Cl.
*G06T 7/00*    (2017.01)
*G06T 7/11*    (2017.01)
(Continued)

(52) U.S. Cl.
CPC .......... *G06T 7/0012* (2013.01); *G06K 9/6256* (2013.01); *G06K 9/6277* (2013.01);
(Continued)

(58) Field of Classification Search
CPC . G06T 2207/10016; G06T 2207/10024; G06T 2207/20084; G06T 3/4092;
(Continued)

(56) References Cited

U.S. PATENT DOCUMENTS

| | | | | |
|---|---|---|---|---|
| 6,298,160 | B1 * | 10/2001 | Goertzen | G06T 9/005 382/232 |
| 2006/0078993 | A1 * | 4/2006 | Phan | A61P 35/00 435/366 |

(Continued)

FOREIGN PATENT DOCUMENTS

WO    2017190743    11/2017

OTHER PUBLICATIONS

Alansary, Amir et al. "Fast Fully Automatic Segmentation of the Human Placenta from Motion Corrupted MRI." Medical Image Computing and Computer-Assisted Intervention. MICCAI 2016, LNCS, vol. 9901, pp. 589-597. Springer, Cham, Oct. 2, 2016, https://doi.org/10.1007/978-3-319-46723-8_68.
(Continued)

*Primary Examiner* — Ajibola A Akinyemi
(74) *Attorney, Agent, or Firm* — Dinsmore & Shohl LLP

(57) ABSTRACT

Systems and methods for completing a morphological characterization of an image of a placenta and providing suggested pathological diagnoses are disclosed. A system includes programming instructions that, when executed, cause processing devices to execute commands according to the following logic modules: an Encoder module that receives the digital image of the placenta and outputs a pyramid of feature maps, a SegDecoder module that seg-
(Continued)

ments the pyramid of feature maps on a fetal side image and on a maternal side image, a Classification Subnet module that classifies the fetal side image and the maternal side image, and a convolutional IPDecoder module that localizes an umbilical cord insertion point of the placenta from the classified fetal side image and the classified maternal side image. The localized umbilical cord insertion point, segmentation maps for the classified fetal side and maternal side images are provided to an external device for determining the morphological characterization.

18 Claims, 17 Drawing Sheets

(51) Int. Cl.
G06K 9/62 (2006.01)
G06N 3/04 (2006.01)

(52) U.S. Cl.
CPC .............. *G06N 3/0454* (2013.01); *G06T 7/11* (2017.01); *G06T 2207/20081* (2013.01); *G06T 2207/20084* (2013.01); *G06T 2207/30004* (2013.01)

(58) Field of Classification Search
CPC . G06T 5/002; G06T 5/009; G06T 7/11; G06T 11/003; G06T 1/0007; G06T 2200/04; G06T 2207/10081; G06T 2207/20072; G06T 2207/20081; G06T 2207/30016; G06T 2207/30101; G06T 2207/30168; G06T 7/0002; G06T 7/0012; G06T 9/005
USPC ....................................................... 382/159
See application file for complete search history.

(56) References Cited

U.S. PATENT DOCUMENTS

| 2008/0248005 A1* | 10/2008 | Phan | C12N 5/0676 424/93.7 |
|---|---|---|---|
| 2009/0244093 A1* | 10/2009 | Chen | G11B 27/28 345/620 |
| 2020/0151546 A1* | 5/2020 | Liu | G06K 9/4628 |

OTHER PUBLICATIONS

Badrinarayanan, Vjay et al. "SegNet: A Deep Convolutional Encoder-Decoder Architecture for Image Segmentation." IEEE Transactions on Pattern Analysis and Machine Intelligence (2017), vol. 39, No. 12, pp. 2481-2495. IEEE, Jan. 2, 2017, DOI: 10.1109/TPAMI.2016. 2644615.
Bi, Jinbo et al. "An Improved Multi-task Learning Approach with Applications in Medical Diagnosis." Machine Learning and Knowledge Discovery in Databases. ECML PKDD (2008), vol. 5211, pp. 117-132. Springer, Berlin, Heidelberg, 2008, https://doi.org/10.1007/978-3-540-87479-9_26.
Chen, Liang-Chieh et al. "DeepLab: Semantic Image Segmentation with Deep Convolutional Nets, Atrous Convolution, and Fully Connected CRFs." IEEE Transactions on Pattern Analysis and Machine Intelligence, Issue 4 (2018): vol. 40, pp. 834-848. IEEE, Apr. 27, 2017, DOI: 10.1109/TPAMI.2017.2699184.
Chen, Yukun et al., "PlacentaNet: Automatic Morphological Characterization of Placenta Photos with Deep Learning," Medical Image Computing and Computer Assisted Intervention. MICCAI 2019, LNCS vol. 11764, pp. 487-495. Springer, Cham, Oct. 10, 2019, https://doi.org/10.1007/978-3-030-32239-7_54.
Cheplygina, Veronika et al. "Not-so-supervised: A survey of semi-supervised, multi-instance, and transfer learning in medical image analysis." Medical Image Analysis (2019), vol. 54, No. pp. 280-296. Elsevier B.V., Mar. 29, 2019, https://doi.org/10.1016/j.media.2019. 03.009.
Christodoulidis, Stergios et al. "Multi-source Transfer Learning with Convolutional Neural Networks for Lung Pattern Analysis." IEEE Journal of Biomedical and Health Informatics (2017), vol. 21, No. 1. IEEE, Dec. 7, 2016, DOI: 10.1109/JBHI.2016.2636929.
Cui, Yin et al. "Class-Balanced Loss Based on Effective Number of Samples." 2019 IEEE/CVF Conference on Computer Vision and Pattern Recognition (CVPR), pp. 9268-9277. IEEE, Jun. 15-20, 2019, DOI: 10.1109/CVPR.2019.00949.
Deng, Jia et al. "ImageNet: A large-scale hierarchical image database." 2009 IEEE Conference on Computer Vision and Pattern Recognition, pp. 248-255. IEEE, Jun. 20-25, 2009, DOI: 10.1109/CVPR.2009.5206848.
Ernst, L.M. et al. "Gross patterns of umbilical cord coiling: correlations with placental histology and stillbirth." Placenta (2013), vol. 34, pp. 583-588. Elsevier Ltd., May 2, 2013, http://dx.doi.org/10.1016/j.placenta.2013.04.002.
Haeussner, E. et al. "Birth weight correlates with size but not shape of the normal human placenta." Placenta (2013), vol. 34, No. 7, pp. 574-582. Elsevier Ltd., May 11, 2013, http://dx.doi.org/10.1016/j.placenta.2013.04.011.
He, Kaiming et al. "Deep Residual Learning for Image Recognition." 2016 IEEE Conference on Computer Vision and Pattern Recognition (CVPR), pp. 770-778. IEEE, Jun. 27-30, 2016, DOI: 10.1109/CVPR.2016.90.
Hwang, Sangheum, et al. "Self-Transfer Learning for Weakly Supervised Lesion Localization." Medical Image Computing and Computer-Assisted Intervention—MICCAI 2016, LNCS 9901, pp. 239-246. Springer International Publishing 2016, Oct. 2, 2016. https://doi.org/10.1007/978-3-319-46723-8_28.
Kaspar, H.G. et al. "The placenta in meconium staining: lesions and early neonatal outcome." Clinical and Experimental Obstetrics & Gynecology (2000), vol. 27, No. 1, pp. 63-66. PubMed, https://pubmed.ncbi.nlm.nih.gov/10758806/.
Khong, Teck Yee et al. "Sampling and Definitions of Placental Lesions: Amsterdam Placental Workshop Group Consensus Statement," Archives of Pathology & Laboratory Medicine (2016), vol. 140, No. 7, pp. 698-713, May 25, 2016, DOI: 10.5858/arpa.2015-0225-CC.
Kidron, Debora et al. "Automated image analysis of placental villi and syncytial knots in histological sections." Placenta (2017), vol. 53, pp. 113-118. Elsevier Ltd., Apr. 8, 2017, DOI: 10.1016/j.placenta. 2017.04.004.
Lin, Tsung-Yi et al. "Focal Loss for Dense Object Detection." 2017 IEEE International Conference on Computer Vision (ICCV). IEEE, Oct. 22-29, 2017, DOI: 10.1109/ICCV.2017.324.
Long, Jonathan et al. "Fully convolutional networks for semantic segmentation," 2015 IEEE Conference on Computer Vision and Pattern Recognition (CVPR). IEEE, Jun. 7-12, 2015, DOI: 10.1109/CVPR.2015.7298965.
Looney, Padraig et al. "Automatic 3D ultrasound segmentation of the first trimester placenta using deep learning." 2017 IEEE 14th International Symposium on Biomedical Imaging (ISBI 2017). IEEE, Apr. 18-21, 2017, DOI: 10.1109/ISBI.2017.7950519.
Malathi, G. et al. "Statistical measurement of ultrasound placenta images complicated by gestational diabetes mellitus using segmentation approach." Journal of Information Hiding and Multimedia Signal Processing (2011), vol. 2, No. 4, pp. 332-343. Ubiquitous International, Oct. 2011, ISSN 2073-4212.
Milletari, Fausto et al. "V-Net: Fully Convolutional Neural Networks for Volumetric Medical Image Segmentation." 2016 Fourth International Conference on 3D Vision (3DV). IEEE, Oct. 25-28, 2016, DOI: 10.1109/3DV.2016.79.
Newell, Alejandro et al. "Stacked Hourglass Networks for Human Pose Estimation." Computer Vision. ECCV 2016, vol. 9912, pp. 483-499. Springer, Cham, Sep. 17, 2016, https://doi.org/10.1007/978-3-319-46484-8_29.

(56) References Cited

OTHER PUBLICATIONS

Pan, Sinno Jialin et al. "A Survey on Transfer Learning." IEEE Transactions on Knowledge and Data Engineering (2010), vol. 22, No. 10, pp. 1345-1359. IEEE, Oct. 16, 2009, DOI: 10.1109/TKDE.2009.191.

Paszke, Adam et al. "PyTorch: An Imperative Style, High-Performance Deep Learning Library." Advances in Neural Information Processing Systems 32. NIPS 2019. http://papers.nips.cc/paper/9015-pytorch-an-imperative-stylehigh-.

Payer, Christian et al. "Integrating spatial configuration into heatmap regression based CNNs for landmark localization." Medical image Analysis (2019), vol. 54, pp. 207-219. Elsevier B.V., Mar. 25, 2019, https://doi.org/10.1016/j.media.2019.03.007.

Redmon, Joseph et al. "You Only Look Once: Unified, Real-Time Object Detection." 2016 IEEE Conference on Computer Vision and Pattern Recognition (CVPR), pp. 779-788 IEEE, Jun. 27-30, 2016, DOI: 10.1109/CVPR.2016.91.

Roberts, Drucilla J. "Placental Pathology, a Survival Guide." Archives of Pathology & Laboratory Medicine, (2008), vol. 132, pp. 641-651.

Ronneberger, Olaf et al. "U-Net: Convolutional Networks for Biomedical Image Segmentation." Medical Image Computing and Computer-Assisted Intervention. MICCAI 2015, vol. 9351, pp. 234-241. Springer, Cham, Nov. 18, 2015, https://doi.org/10.1007/978-3-31 9-24574-4_28.

Salafia, Carolyn M. et al. "Placental surface shape, function, and effects of maternal and fetal vascular pathology." Placenta (2010), vol. 31, No. 11, pp. 958-962. Elsevier Ltd., Nov. 2010, https://doi.org/10.1016/j.placenta.2010.09.005.

Shin, Hoo-Chang et al. "Deep Convolutional Neural Networks for Computer-Aided Detection: CNN Architectures, Dataset Characteristics and Transfer Learning." IEEE Transactions on Medical Imaging (2016), vol. 35, No. 5, pp. 1285-1298. IEEE, Feb. 11, 2016. DOI: 10.1109/TMI.2016.2528162.

Silver, Robert M. "Abnormal Placentation: Placenta Previa, Vasa Previa, and Placenta Accreta." Obstetrics & Gynecology, Sep. 2015, vol. 126, No. 3, pp. 654-668. doi: 10.1097/AOG.0000000000001005.

Thomas, Kristine A. et al. "Unsupervised Segmentation for Inflammation Detection in Histopathology Images," Image and Signal Processing. International Conference on Image and Signal Processing (2010), vol. 6134, pp. 541-549. Springer-Verlag Berlin Heidelberg 2010, Jun. 30, 2010, DOI: 10.1007/978-3-642-13681-8_63.

Tompson, Jonathan J. et al. "Joint Training of a Convolutional Network and a Graphical Model for Human Pose Estimation." Advances in Neural Information Processing Systems 27. NIPS 2014, pp. 1799-1807. http://papers.nips.cc/paper/5573-joint-training-of-a-convolutional-network-and-a-graphical-model-for-human-pose-estimation.

Yampolsky, Michael et al. "Modeling the variability of shapes of a human placenta." Placenta (2008), vol. 29, No. 9, pp. 790-797. Elsevier Ltd., Dec. 20, 2007, https://doi.org/10.1016/j.placenta.2008.06.005.

Yampolsky, Michael et al. "Centrality of the Umbilical Cord Insertion in a Human Placenta Influences the Placental Efficiency." Placenta (2009), vol. 30, No. 12, pp. 1058-1064. Elsevier Ltd., Oct. 30, 2009, https://doi.org/10.1016/j.placenta.2009.10.001.

Zhang, Wenlu et al. "Deep Model Based Transfer and Multi-Task Learning for Biological Image Analysis." IEEE Transactions on Big Data (2020), vol. 6, No. 2, pp. 322-333. IEEE, May 30, 2016, DOI: 10.1109/TBDATA.2016.2573280.

\* cited by examiner

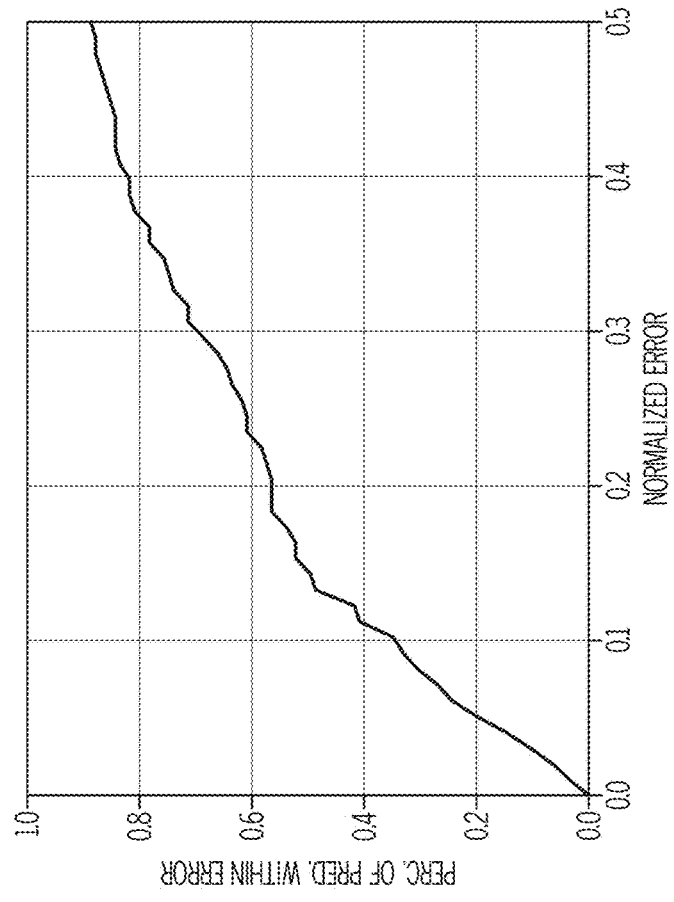
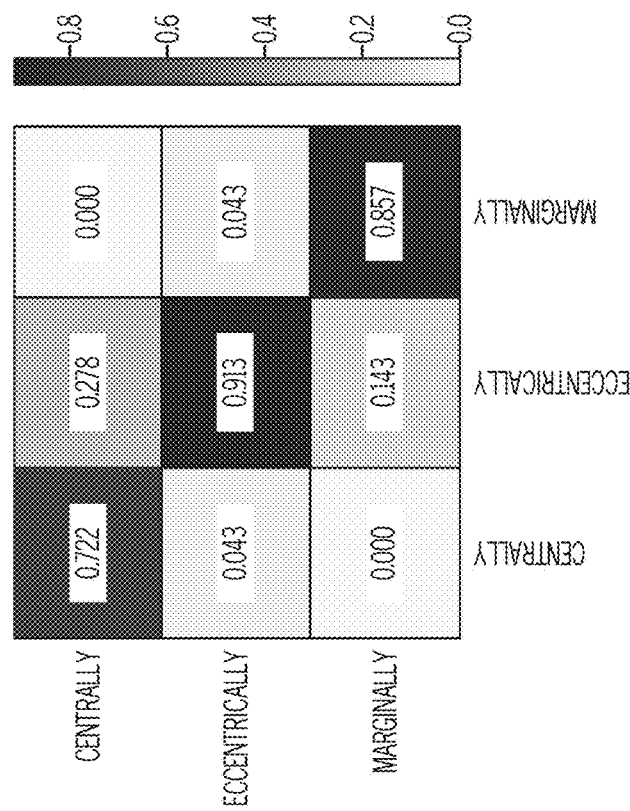
FIG. 11A
FIG. 11B

SYSTEMS AND METHODS UTILIZING ARTIFICIAL INTELLIGENCE FOR PLACENTAL ASSESSMENT AND EXAMINATION

CROSS-REFERENCE TO RELATED APPLICATION

The present disclosure claims the benefit of priority to U.S. Provisional Application No. 62/888,838, filed Aug. 19, 2019 and entitled "AI-BASED PLACENTA ASSESSMENT AND EXAMINATION," the entire contents of which is incorporated herein in its entirety.

BACKGROUND

Field

The present disclosure generally relates to image analysis systems and methods, and more specifically, to systems and methods that analyze images of placentas using artificial intelligence to assess and examine the placentas.

Technical Background

The placenta is a window into the events of a pregnancy and the health of the mother and baby. However, a very small percentage of placentas around the world are ever examined by a pathologist. Even in developed countries like the U.S., placentas are examined and characterized by a pathologist only when it is considered necessary and resources are available. Full pathological examination is expensive and time consuming. Pathologists or pathologist assistants perform a macroscopic or gross examination and select sections for microscopic examination. After processing, they examine sections under a microscope and produce a written report that contains various measurements (e.g., the weight, the disc diameter) and diagnoses (e.g., completeness or retained placenta, cord insertion type, shape category, meconium, chorioamnionitis, and/or the like). In some specialty centers the gross examination may include photography using specialized imaging equipment. These measurements and placental diagnoses can be useful for both short-term and long-term clinical care of the mother and baby.

SUMMARY

In an aspect, a system for completing a morphological characterization of a digital image of a placenta includes one or more processing devices and one or more non-transitory, processor-readable storage mediums having programming instructions thereon that, when executed, cause the one or more processing devices to execute commands according to the following logic modules: an Encoder module that receives the digital image of the placenta and outputs a pyramid of feature maps, a SegDecoder module that segments the pyramid of feature maps on a fetal side image and on a maternal side image, a Classification Subnet module that classifies the fetal side image and the maternal side image, and a convolutional IPDecoder module that localizes an umbilical cord insertion point of the placenta from the classified fetal side image and the classified maternal side image. The localized umbilical cord insertion point, a segmentation map for the classified fetal side image, and a segmentation map for the classified maternal side image are provided to an external device for the purposes of determining the morphological characterization by the external device.

In another aspect, a system for providing a suggested pathological diagnosis of a placenta based on image data pertaining to the placenta includes one or more processing devices and one or more non-transitory, processor-readable storage mediums having programming instructions thereon that, when executed, cause the one or more processing devices to receive the image data pertaining to the placenta from a morphological characterization system, extract a first segmentation map for a classified fetal side image of the placenta and a second segmentation map for a classified maternal side image of the placenta from the image data, determine, from the first segmentation map and the second segmentation map, pixels pertaining to a target portion to obtain a processed placenta photo, transmit the processed placenta photo to a neural network together with a set of instructions for determining one or more features of the target portion, receive an output from the neural network that comprises a determined pathological diagnosis from the one or more features of the target portion, and provide the determined pathological diagnosis to an external device as a suggested pathological diagnosis of the placenta.

Additional features and advantages of the aspects described herein will be set forth in the detailed description which follows, and in part will be readily apparent to those skilled in the art from that description or recognized by practicing the aspects described herein, including the detailed descript which follows, the claims, as well as the appended drawings.

It is to be understood that both the foregoing general description and the following detailed description describe various aspects and are intended to provide an overview or framework for understanding the nature and character of the claimed subject matter. The accompanying drawings are included to provide a further understanding of the various aspects, and are incorporated into and constitute a part of this specification. The drawings illustrate the various aspects described herein, and together with the description serve to explain the principles and operations of the claimed subject matter.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 11A depicts an illustrative confusion matrix for an insertion type categorization according to one or more embodiments shown and described herein;

FIG. 11B depicts a plot of an illustrative quantitative evaluation of an estimation on the distance from an insertion point to a nearest disc margin according to one or more embodiments shown and described herein;

DETAILED DESCRIPTION

Figure 1:
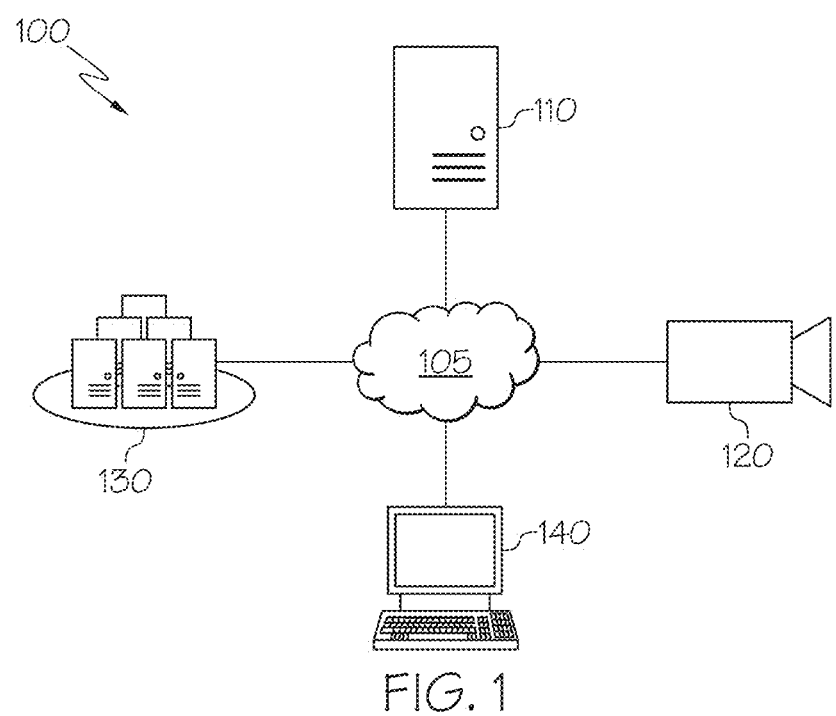
FIG. 1 schematically depicts an illustrative placental assessment system according to one or more embodiments shown and described herein.

Reference will now be made in detail to various aspects of systems and methods for analyzing placentas, examples of which are illustrated in the accompanying drawings. Whenever possible, the same reference numerals will be sued throughout the drawings to refer to the same or like parts.

The present disclosure generally relates to systems and methods of automatically assessing placentas utilizing artificial intelligence to analyze image data pertaining to the placentas. The systems and methods described herein generally include addressing morphological characterization, which includes the tasks of placental image segmentation, umbilical cord insertion point localization, and maternal/fetal side classification. The systems and methods described herein also utilize clinically meaningful feature analyses of placentas, which comprises detection of retained placenta (e.g., incomplete placenta), umbilical cord knot, meconium, abruption, chorioamnionitis, and hypercoiled cord, and categorization of umbilical cord insertion type. The systems and methods described herein curate a dataset including about 1,300 placenta images with hand-labeled pixel-level segmentation map, cord insertion point and other information extracted from the associated pathology reports. The systems and methods further utilize an AI-based Placental Assessment and Examination system (AI-PLAX), which is a two-stage photograph-based pipeline for fully automated analysis. In a first stage, a three encoder-decoder convolutional neural network with a shared encoder is used to address morphological characterization tasks by employing a transfer-learning training strategy. In a second stage, distinct sub-models are employed to solve different feature analysis tasks by using both the photograph and the output of the first stage. The effectiveness of the pipeline is evaluated by using the curated dataset as well as the pathology reports in the medical record. Through extensive experiments, it is demonstrated herein that the systems and methods are able to produce accurate morphological characterization and very promising performance on aforementioned feature analysis tasks, all of which may possess clinical impact and contribute to future pregnancy research.

Automated placental assessment based on photographic imaging can potentially allow more placentas to be examined, reduce the number of normal placentas sent for full pathological examination, and provide more accurate and timely morphological and pathological measurements or analyses. Typical photographs of the placentas capture the umbilical cord inserting into the fetal side of the disc, as well as the maternal side appearance. The systems and methods described herein focus on a fully automated system for placental assessment and examination. Specifically, such systems will be responsible for placental segmentation, umbilical insertion point localization, fetal/maternal side classification, and the prediction of a number of pathological indicators (e.g., gross abnormality). These indicators include retained placenta (e.g., incomplete placenta), umbilical cord knot, meconium, abruption, chorioamnionitis, hypercoiled cord, and umbilical cord insertion type. Some pathological findings from placentas are strictly microscopic; however, many have gross (macroscopic) and microscopic features, while some are only seen on gross exam. The latter are particularly frequent in placental pathology. Thus, a focus of the present disclosure includes, but is not limited to, predicting macroscopic pathological indicators.

Existing placental imaging research can be classified into two types based on the time the image is taken: pre-delivery and post-delivery. Because a photo for the placenta under visible light spectrum cannot be captured prior to the delivery, pre-delivery placental imaging research has been focused on images obtained through other means, such as, for example, MRI and ultrasound. Pre-delivery placental imaging research focuses on segmentation, which can be used as visual aids for doctors.

Post-delivery placental imaging research engages different methods and thus can be further categorized into two types: those using microscopic images and those using macroscopic images of the placenta taken by cameras. While microscopic assessment is more established, it requires equipment and personnel to make slides and microscopes and microphotography to make images. In contrast, camera-based imaging in the second category only requires an ordinary camera or even a camera phone, and thus has greater potential to be widely adopted. Current macroscopic placental assessment from photos focus on a specific aspect and involved human assessment as a part of the process. For example, some assessments include studying variations in disc surface shape and vascular network from placental photos to identify associations between these factors and vascular pathologies and placental efficiency. Others attempt to estimate the size and shape of placentas from photos and found placenta size but not shape to have an association with the birth weight. Currently, there has not been an automated approach to analyze placenta photographs. Such an approach has the potential for widespread adoption because today's smartphones have high-quality cameras as well as highly capable CPU, GPU, and/or AI chips.

The systems and methods described herein present a two-stage pipeline for automated placental assessment and examination using photos. In the first stage (Stage I), we take a transfer learning (TL) approach to tackle the associated tasks of morphological characterization rather than employing an independent model for each task. Transfer learning promises performance gain and robustness enhancement through representation sharing for closely related tasks. The use of transfer learning may be summarized into three categories: "same domain, different tasks", "different domains, same task" and "different domains, different tasks". The systems and methods described herein are closest to the "same domain, different tasks" category but is not an exact match. More precisely, our method should fall into a category described as "similar/overlapped domains, different tasks" because the source and target domains have overlap but are not the same, as described in greater detail herein. Specifically, we transfer the learned representation of the encoder from the segmentation task to the other two tasks, e.g. disc side classification and insertion point localization. Our network architecture design takes inspiration from the recent deep learning advances on classification, image, and key point localization. In particular, the design of our segmentation module follows the practice of concatenating feature maps in encoder with feature maps in decoder, such as performed in the U-Net; and the design of our insertion point module follows the practice of regressing a Gaussian heat map, rather than using the coordinate values, as the ground truth, which has been shown to be successful in human key-point/joint localization tasks. In some embodiments, intermediate supervision may be important to improving localization accuracy. Such an idea is taken in our design by considering two heat map predictions in the final loss—one from the final feature layer and one from the intermediate feature layer. In the second stage (Stage II), we employ independent models each tailored for an individual task for a few important placental assessment tasks including but not limited to detection of retained placenta (e.g., incomplete placenta), umbilical cord knot, meconium, abruption, chorioamnionitis, hypercoiled cord, and categorization of umbilical cord insertion type.

We chose to pursue a two-stage pipeline based on the following observations, both of which make it difficult to build an end-to-end model for all tasks: (1) Almost all of our second-stage tasks only apply to either the fetal side or the maternal side of a placenta or only to the disc/cord/ruler region; and (2) A relatively small fraction of all images bears the abnormalities we attempt to detect for the tasks in the second stage, and the sets of images bearing different abnormalities often have little overlap.

The first observation makes it natural for the second-stage tasks to take in the segmentation and disc-side predictions from the first stage to narrow down the region of interest and eliminate irrelevant information. Also, this means the input feature space for these tasks is rather different from the first stage or other second-stage tasks, and it is difficult, if not impossible, to apply transfer learning here to let those tasks benefit from the representations learnt from other tasks. In contrast, tasks in the first stage are more closely related and have larger overlapped input feature space. The second observation makes it sometimes impractical to use the same training/testing set for all tasks. Each task may have its own training/testing set such that the model will not be dominated by negative cases (e.g., without abnormalities).

We summarize the primary contributions as follows. We introduce a novel pipeline for comprehensive, automated placental assessment and examination using photos. The design of the pipeline, which has two stages, takes the relationship and the similarity of the tasks into consideration. Specifically, we use transfer learning to boost performance and robustness for closely related tasks with significant overlapped input space in the first stage. In the second stage, we use the first-stage predictions in separate models to address distinct tasks: to determine if an image is relevant (through side classification) and to provide the region of interest (through segmentation). Our method is explainable by design and achieves highly promising results. We believe isolating the models for irrelevant tasks and enforcing strong priors on the information flow between sub-models are critical under a limited label and robustness-prioritized setting, which is typical for medical image analysis. Such isolation is necessary to reduce the possibility of learning signals/correlations that do not hold true for the general distribution but just happen to be the case in our collected data based on prior domain knowledge. Additionally, distinct sub-models in the second stage can be developed in parallel and can be upgraded without worrying that it will affect performance for other tasks. Our use of transfer learning for the first-stage tasks can be categorized into the "similar/overlapped domains, different tasks" type, which is novel and can be applied to other medical image analysis problems. We curated a first-of-its-kind large-scale dataset with hand-labeled segmentation maps, umbilical cord insertion point location and diagnoses extracted from the associated pathology reports. This dataset enabled us to develop our computational pipeline addressing automated placental assessment and examination tasks. We believe the dataset will also be highly beneficial to future research on the placenta and adverse prenatal and postpartum outcomes.

The term "segmentation map" as used herein generally refers to a map from image data that shows how each pixel in the image data is associated with a semantic category, such as the various semantic categories described herein (e.g. disc, cord, ruler, background). That is, the segmentation maps described herein may show how each pixel in the image data is associated with a disc, how each pixel in the image data is associated with an umbilical cord, how each pixel in the image data is associated with a ruler, and/or how each pixel in the image data is associated with background.

Turning now to FIG. 1, an illustrative system 100 of utilizing artificial intelligence for placental assessment and examination is depicted. The system 100, includes, but is not limited to, a network 105 that is generally configured to electronically connect one or more systems, devices, and/or components. Illustrative examples of systems, devices, and/or components that may be electronically connected to the network 105 include, but are not limited to, a server computing device 110, an imaging device 120, a user computing device 140, and an artificial intelligence system 130. While FIG. 1 only depicts a single server computing device 110, a single imaging device 120, a single user computing device 140, and a single artificial intelligence system 130, the present disclosure is not limited to such. That is, the system may include one or more server computing devices 110, one or more imaging devices 120, one or more user computing devices 140, and/or one or more artificial intelligence systems 130 in other embodiments.

The network 105 may include any network now known or later developed, including, but not limited to, a wide area network (WAN), such as the Internet, a local area network (LAN), a mobile communications network, a public service telephone network (PSTN), a personal area network (PAN), a metropolitan area network (MAN), a virtual private network (VPN), or any combination thereof.

The server computing device 110 is generally a computing device that contains components for executing various processes, such as receiving data, cataloging data, cross-referencing data, recording data, providing data, generating data, executing image recognition processes, executing assessment processes, executing examination processes, hosting applications, providing user interfaces, interacting with applications located on other devices, and/or the like according to embodiments shown and described herein. That is, the server computing device 110 may include at least one or more processing devices and a non-transitory memory component, where the non-transitory memory component includes programming instructions that cause the one or more processing devices to execute the various processes described herein. In some embodiments, server computing device 110 may include a data storage component that is used for storing data, such as the data described herein. In some embodiments, server computing device 110 may include networking hardware that is used for communicating with the various components of the system 100. Additional details regarding the server computing device 100 will be described herein with respect to FIGS. 2A-2B.

The imaging device 120 is not limited by this disclosure, and may generally be any device that captures images. In some embodiments, the imaging device 120 may have optical components for sensing and capturing images in the visible spectrum. In other embodiments, the imaging device 120 may be particularly configured to sense electromagnetic radiation (e.g., thermal radiation). Accordingly, the imaging device 120 may generally be a device particularly tuned or otherwise configured to obtain images in spectra where particular types of radiation is readily detected, such as the visible spectrum and the infrared spectrum (including the far infrared and the near infrared spectrum). As such, one illustrative example of a device particularly tuned or otherwise configured to obtain images in spectra where heat radiation includes, but is not limited to, an infrared camera. In some embodiments, the imaging device 120 may be a camera that is sensitive within a range of wavelengths of about 0.38 micrometer ($\mu$m) to about 14 $\mu$m, including about 0.38 $\mu$m, about 0.45 $\mu$m, about 0.485 $\mu$m, about 0.5 $\mu$m, about 0.565 $\mu$m, about 0.59 $\mu$m, about 0.625 $\mu$m, about 0.74 $\mu$m, about 1 $\mu$m, about 2 $\mu$m, about 3 $\mu$m, about 4 $\mu$m, about 5 $\mu$m, about 6 $\mu$m, about 7 $\mu$m, about 8 $\mu$m, about 9 $\mu$m, about 10 $\mu$m, about 11 $\mu$m, about 12 $\mu$m, about 13 $\mu$m, about 14 $\mu$m, or any value or range between any two of these values (including endpoints). In certain embodiments, the imaging device 120 may be a multispectral camera. Illustrative examples of suitable devices that may be used for the imaging device 114 include, but are not limited to, an IR-camera (Infrared-camera), NIR-camera (Near Infrared-camera), a VISNIR-camera (Visual Near Infrared-camera), a CCD camera (Charged Coupled Device-camera), and a CMOS-camera (Complementary Metal Oxide Semiconductor-camera).

In some embodiments, the imaging device 120 may have a monochrome image sensor. In other embodiments, the imaging device 120 may have a color image sensor. In various embodiments, the imaging device 120 may include one or more optical elements, such as lenses, filters, and/or the like. In some embodiments, the imaging device 120 may further be a device particularly configured to provide signals and/or data corresponding to the sensed electromagnetic radiation to the control component 120. As such, the imaging device 114 may be communicatively coupled to the control component 120, as indicated by the dashed lines depicted in FIG. 1 between the imaging device 114 and the control component 120. In some embodiments, the imaging device 114 may have a 3D depth image sensor.

In various embodiments, the imaging device 120 may be positioned to capture placenta images, such as the images described herein. That is, the imaging device 120 may generally be positioned such that a field of view of the imaging device 120 captures at least a portion of a surface supporting a placenta and/or other objects. In some embodiments, the imaging device 120 may be mounted to any stationary or moving apparatus that provides the imaging device with the capability of imaging the placenta as described herein. For example, the imaging device 120 may be coupled to an arm or other support (not shown) that allows the imaging device 120 to move about an axis A around the placenta such that the imaging device 12 can capture any angle of the placenta. In some embodiments, movement of the imaging device 120 may be controlled (e.g., remote controlled) by a user.

The user device 140 may generally provide an interface between a user and the other components connected to the network 105, including other users and/or other user computing devices. Thus, the user device 140 may be used to perform one or more user-facing functions, such as receiving one or more inputs from a user or providing information to the user. The user device 140 may also be used to input additional data into any data storage components of the systems, devices, and/or components of the system 100. The user device 140 may also be used to perform one or more of the processes described herein. In some embodiments, the user device 140 may be used to supply one or more of a placenta image, assessment information, and examination results using an output device, such as a display, one or more radios, and/or the like, as described in greater detail herein.

It should be understood that while the user device 140 is depicted as a personal computing device, this is a nonlimiting example. More specifically, in some embodiments, any type of computing device (e.g., mobile device, tablet computing device, personal computer, server, etc.) may be used for any of these components.

The artificial intelligence system 130 is generally one or more computing devices (e.g., a collection of computing devices) that contain hardware and software programming for hosting and operating one or more artificial intelligence algorithms. The one or more artificial intelligence algorithms may generally be trained on existing data in such a way that, when new data is received (e.g., new image data pertaining to a placenta, as described herein), particular characteristics of the new data can be determined and provided. For example, the algorithms hosted and operated by the artificial intelligence system 130 may receive image data pertaining to a placenta, categorize one or more features based on the image data, assess the placenta in the image based on the one or more categorized features, and/or the like, as described in greater detail herein.

While each of these computing devices is illustrated in FIG. 1 as a single piece of hardware, this is also merely an example. More specifically, each of the components depicted in FIG. 1 may represent a plurality of computers, servers, databases, components, and/or the like.

Figure 2A:
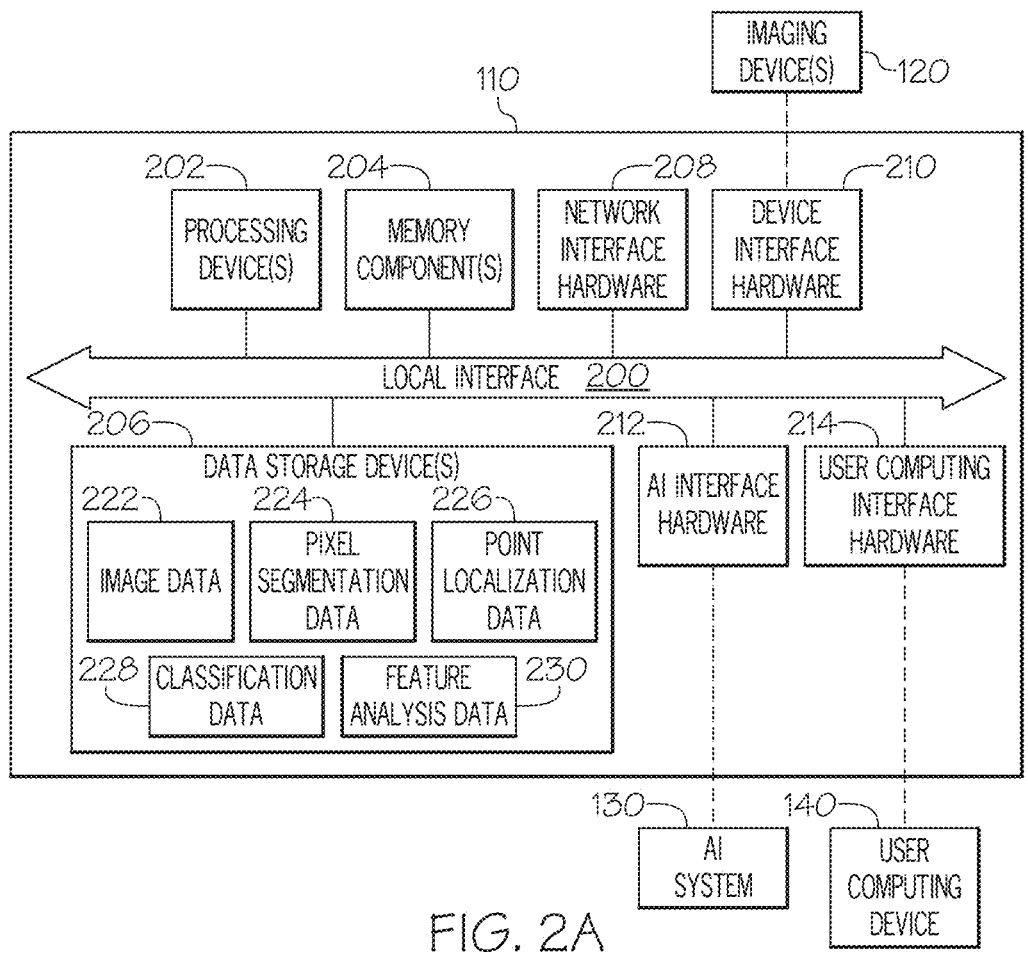
FIG. 2A depicts a block diagram of illustrative hardware components located within a placental assessment device according to one or more embodiments shown and described herein.

Illustrative hardware components of the server computing device 110 is depicted in FIG. 2A. While the hardware components of the server computer device 110 are shown and described, the present disclosure is not limited to such. For example, similar hardware components may also be included within any one of the various other systems, devices, and/or components of the system 100, including, but not limited to, the imaging device 120, the user computing device 140, and/or the artificial intelligence system 130.

A local interface 200 may interconnect the various components of the server computing device 110. The local interface 200 may be formed from any medium that is capable of transmitting a signal such as, for example, conductive wires, conductive traces, optical waveguides, or the like. Moreover, the local interface 200 may be formed from a combination of mediums capable of transmitting signals. In one embodiment, the local interface 200 includes a combination of conductive traces, conductive wires, connectors, and buses that cooperate to permit the transmission of electrical data signals to components such as processors, memories, sensors, input devices, output devices, and communication devices. Accordingly, the local interface 200 may include a bus. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium. The local interface 200 communicatively couples the various components of the server computing device 110.

One or more processing devices 202, such as a computer processing unit (CPU), may be the central processing unit(s) of the computing device, performing calculations and logic operations required to execute a program. Each of the one or more processing devices 202, alone or in conjunction with one or more of the other elements disclosed in FIG. 2A, is an illustrative processing device, computing device, processor, or combination thereof, as such terms are used within this disclosure. Accordingly, each of the one or more processing devices 202 may be a controller, an integrated circuit, a microchip, a computer, or any other computing device. The one or more processing devices 202 are communicatively coupled to the other components of the server computing device 110 by the local interface 200.

One or more memory components 204 configured as volatile and/or nonvolatile memory, such as read only memory (ROM) and random access memory (RAM; e.g., including SRAM, DRAM, and/or other types of RAM), flash memories, hard drives, secure digital (SD) memory, registers, compact discs (CD), digital versatile discs (DVD), Blu-Ray™ discs, or any non-transitory memory device capable of storing machine-readable instructions may constitute illustrative memory devices (i.e., non-transitory processor-readable storage media) that is accessible by the one or more processing devices 202. Such memory components 204 may include one or more programming instructions thereon that, when executed by the one or more processing devices 202, cause the one or more processing devices 202 to complete various processes, such as the processes described herein. Depending on the particular embodiment, these non-transitory computer-readable mediums may reside within the server computing device 110 and/or external to the server computing device 110. A machine-readable instruction set may include logic or algorithm(s) written in any programming language of any generation (e.g., 1GL, 2GL, 3GL, 4GL, or 5GL) such as, for example, machine language that may be directly executed by the one or more processing devices 202, or assembly language, object-oriented programming (OOP), scripting languages, microcode, and/or the like that may be compiled or assembled into machine readable instructions and stored in the non-transitory computer readable memory (e.g., the memory components 204). Alternatively, a machine-readable instruction set may be written in a hardware description language (HDL), such as logic implemented via either a field-programmable gate array (FPGA) configuration or an application-specific integrated circuit (ASIC), or their equivalents. Accordingly, the functionality described herein may be implemented in any conventional computer programming language, as preprogrammed hardware elements, or as a combination of hardware and software components.

In some embodiments, the program instructions contained on the one or more memory components 204 may be embodied as a plurality of software modules, where each module provides programming instructions for completing one or more tasks. For example, referring now to FIG. 2B, the one or more memory components 204 may contain one or more of operating logic 240, segmentation logic 242, insertion point localization logic 244, classification logic 246, placenta detection logic 248, knot detection logic 250, meconium detection logic 252, umbilical cord insertion type categorization logic 254, and/or hypercoiled cord detection logic 256. The operating logic 240 may include an operating system and/or other software for managing components of the server computing device 110. The segmentation logic 242 may include programming instructions or the like for segmenting image data, as described in greater detail herein. The insertion point localization logic 244 may include programming instructions or the like for localizing an umbilical cord insertion point, as described herein. The classification logic 246 may include programming instructions or the like for maternal/fetal side classification, as described herein. The placenta detection logic 248 may include programming instructions or the like for detecting a placenta from image data, as described herein. The knot detection logic 250 may include programming instructions or the like for detecting an umbilical cord knot from image data, as described herein. The meconium detection logic 252 may include programming instructions or the like for detecting meconium from image data, as described herein. The umbilical cord insertion type categorization logic 254 may include programming instructions or the like for classifying an umbilical cord by insertion type, as described herein. The hypercoiled cord detection logic 256 may include programming instructions for determining that an umbilical cord is hypercoiled from image data, as described in greater detail herein.

The various logic modules described herein with respect to one or more memory components 204 of the server computing device 110 are merely illustrative, and that other logic modules, including logic modules that combine the functionality of two or more of the modules described hereinabove, may be used without departing from the scope of the present application. Furthermore, various logic modules that are specific to other systems, devices, and/or components of the system 100 of FIG. 1 are also contemplated.

Referring again to FIG. 2A, one or more data storage devices 206, which may each generally be a storage medium that is separate from the one or more memory components 204, may contain a data repository for storing data that is used for storing electronic data and/or the like relating to various data generated, captured, and/or the like, as described herein. The one or more data storage devices 206 may be any physical storage medium, including, but not limited to, a hard disk drive (HDD), memory, removable storage, and/or the like. While the one or more data storage devices 206 are depicted as local devices, it should be understood that at least one of the one or more data storage devices 206 may be a remote storage device, such as, for example, a server computing device or the like in some embodiments.

Illustrative data that may be contained within the one or more data storage devices 206 may include, but is not limited to, image data 222, pixel segmentation data 224, point localization data 226, classification data 228, feature analysis data 230, and/or the like. The image data 222 may include, for example, data generated as a result of imaging processes completed by the imaging device 120 (FIG. 1), data provided from external image repositories, and/or the like, as described herein. Still referring to FIG. 2A, the pixel segmentation data 224 may generally be data that is generated as a result of one or more pixel segmentation processes as described herein. The point localization data 226 may generally be data that is generated as the result of one or more point localization processes and/or data that is used for the purposes of executing one or more point localization processes, as described herein. The classification data 228 may be data that is generated as a result of one or more classification processes and/or data that is used by one or more classification processes (e.g., reference data), as described herein. The feature analysis data 230 may be data that is generated as a result of one or more feature analysis processes and/or data that is used by one or more feature analysis processes (e.g., reference data), as described herein.

The types of data described herein with respect to one or more data storage devices 206 of the server computing device 110 are merely illustrative, and that types of data may be used without departing from the scope of the present application. Furthermore, various types of data that are specific to other systems, devices, and/or components of the system 100 of FIG. 1 are also contemplated, such as data that is specific to the imaging device 120, data that is specific to the user device 140 (e.g., user related data), data that is specific to the artificial intelligence system 130 (e.g., data generated as a result of, or to facilitate the operation of one or more artificial intelligence algorithms and/or one or more machine learning algorithms).

Network interface hardware 208 may generally provide the server computing device 110 with an ability to interface with one or more external components of the network 105 (FIG. 1), including one or more devices coupled to the network 205 via the Internet, an intranet, or the like. Still referring to FIG. 2A, communication with external devices may occur using various communication ports (not shown). An illustrative communication port may be attached to a communications network, such as the Internet, an intranet, a local network, a direct connection, and/or the like.

Device interface hardware 210 may generally provide the server computing device 110 with an ability to interface with one or more imaging devices 120, including a direct interface (e.g., not via network 105 depicted in FIG. 1). Still referring to FIG. 2A, communication with such components may occur using various communication ports (not shown). An illustrative communication port may be attached to a communications network, such as the Internet, an intranet, a local network, a direct connection, and/or the like.

AI interface hardware 212 may generally provide the server computing device 110 with an ability to interface with the artificial intelligence (AI) system 130, including a direct interface (e.g., not via network 105 depicted in FIG. 1). Still referring to FIG. 2A, communication with such components may occur using various communication ports (not shown). An illustrative communication port may be attached to a communications network, such as the Internet, an intranet, a local network, a direct connection, and/or the like.

User device interface hardware 214 may generally provide the server computing device 110 with an ability to interface with the user interface computing device 140, including a direct interface (e.g., not via network 105 depicted in FIG. 1). Still referring to FIG. 2A, communication with such components may occur using various communication ports (not shown). An illustrative communication port may be attached to a communications network, such as the Internet, an intranet, a local network, a direct connection, and/or the like.

It should be understood that in some embodiments, the network interface hardware 208, the device interface hardware 210, the AI interface hardware 212, and/or the user device interface hardware 214 may be combined into a single device that allows for communications with other systems, devices, and/or components, regardless of location of such other systems, devices, and/or components.

It should be understood that the components illustrated in FIG. 2A are merely illustrative and are not intended to limit the scope of this disclosure. More specifically, while the components in FIG. 2 are illustrated as residing within the server computing device 110, these are nonlimiting examples. In some embodiments, one or more of the components may reside external to server computing device 110. Similarly, one or more of the components may be embodied in other computing devices not specifically described herein.

Figure 2B:
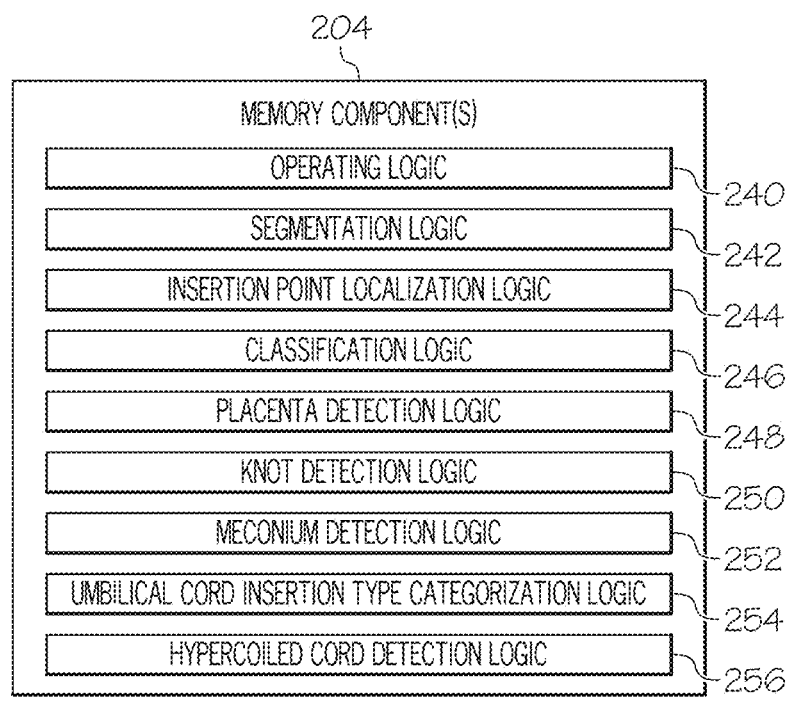
FIG. 2B depicts a block diagram of illustrative logic modules contained within one or more memory components of a placental assessment device according to one or more embodiments shown and described herein.

The systems, devices, and/or components described herein with respect to FIGS. 1 and 2A-2B generally provide functionality for carrying out a plurality of processes for determining placenta and placenta related characteristics from image data, as described herein. The remaining description provided herein includes specific details with respect to such processes.

Dataset

We collected a dataset including 18,400 placenta photos as well as the associated pathology reports written in natural English by the pathologist who originally examined the placenta, spanning the years of 2016 to 2018. The photos and reports are from Northwestern Memorial Hospital, a large urban academic medical center. The photos were taken by on-site pathologists and pathologist assistants using a camera installed on a fixed height arm against standardized blue background. Pathology classification is standardized, and the pathologists have perinatal training and expertise. From the 18,400 placenta photos (of about 9,000 placentas), 1,370 photos were selected to be hand labeled. 665 of the photos are fetal-side images, and 705 are maternal-side images. We developed a web-based tool to collect the following data: i) the pixel-wise segmentation maps, ii) the side-type label as fetal side or maternal side, and iii) the cord insertion point (only for fetal side, visualized as a Gaussian heat map centered at the marked coordinate) so that multiple trained labelers could annotate this dataset concurrently. We also extract diagnoses from the pathology reports. A complete list of diagnoses we extracted from the pathology reports are listed in Appendix A. For those placentas being diagnosed with being retained/incomplete the pixel-wise incomplete area was annotated by a highly-trained pathologist who is a research member (J.A.G.). For true knot in the cord, trained research members placed a bounding box around the knot with expert review as needed.

We divided the fully-labeled dataset into training and testing sets with the ratio of 0.8:0.2. Because the insertion point can only be observed from the fetal side, we only use the 665 fetal-side images for insertion point prediction, with the same training-testing ratio as aforementioned.

Stage I: Morphological Characterization

Figure 3:
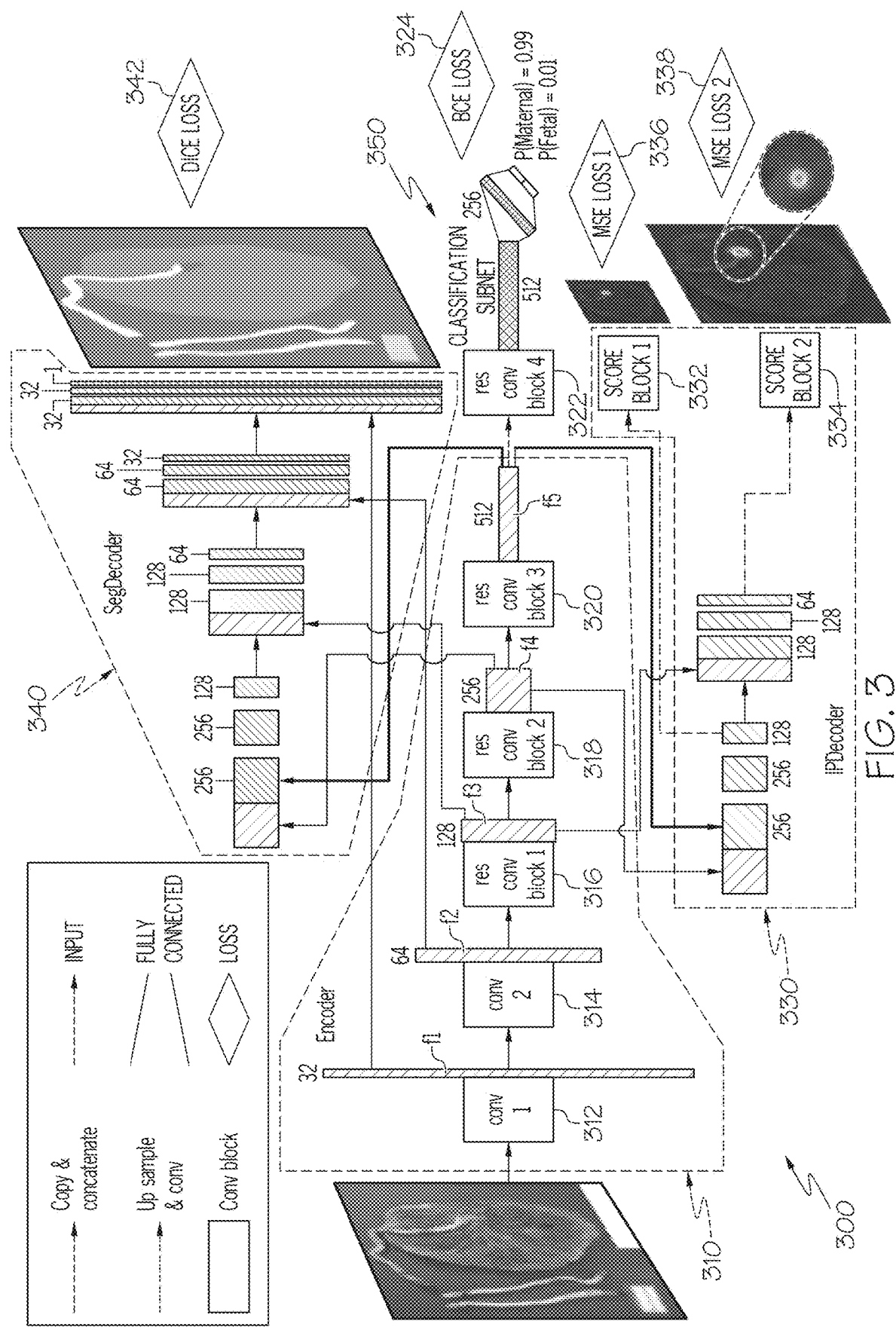
FIG. 3 schematically depicts a flow diagram of an architecture for a model for morphological characterization of placentas according to one or more embodiments shown and described herein.

The proposed model for morphological characterization 300, as illustrated in FIG. 3, includes an Encoder 310 for feature pyramid extraction, which is shared among all tasks, a fully convolutional SegDecoder 340 for placenta image segmentation on both fetal-side and maternal-side images, a Classification Subnet 350 for fetal-side and maternal-side classification, and a fully convolutional IPDecoder 330 for insertion point localization. In some embodiments, the Encoder 310, the SegDecoder 340, the Classification Subnet 350 and the IPDecoder 330 may each be embodied as logic modules contained within the one or more memory components 204 (FIG. 2).

Encoder as Feature Pyramid Extractor

The Encoder 310 takes a placenta image x (either the fetal side or the maternal side) as the input and then outputs a pyramid of feature maps $\{f_1, f_2, f_3, f_4, f_5\}$.

Depending on the tasks, all or part of the feature maps are used by further task modules. Specifically, SegDecoder 340 takes $\{f_1, f_2, f_3, f_4, f_5\}$ as input; Classification Subnet 350 takes $\{f_5\}$ as input; and IPDecoder 330 takes $\{f_3, f_4, f_5\}$ as input. The Conv-1 and Conv-2 blocks (blocks 312 and 314, respectively) both include a Conv-BatchNorm-Relu layer. The difference, however, is that the Cony layer in the Conv-1 block (block 312) has stride 1, while the Cony layer in Conv-2 block (block 314) has stride 2. The Res cony blocks (e.g., block 316, block 318, and block 320) are residual blocks with two convolutional layers with stride 2 and 1, respectively, and the same kernel size 3×3, each of which spatially downsamples the input feature maps to half of its size and doubles the number of feature channels. The residual structure is helpful for training deep architectures.

SegDecoder for Segmentation

Our SegDecoder module 340 includes four expanding fully convolutional blocks, each of which takes the concatenation of a copy of the corresponding feature map $f_i$, i∈{1,2,3,4}, and transposes a convoluted (up-scaling factor 2) output feature map of the last layer. Finally, we apply soft-max to predict the probability of pixel (i,j) being of class k, denoted as p(i,j,k). To overcome the problem of highly imbalanced number of pixels for different categories, we use dice loss (block 342) instead of the common cross entropy loss. Since we have four classes, we adjust the dice loss to suit the 4-class scenario:

$$L^{seg} = 1 - \frac{\sum_{i,j}\sum_{k=0}^{3} p(i,j,k) \cdot g(i,j,k)}{\sum_{i,j}\sum_{k=0}^{3} p^2(i,j,k) + g^2(i,j,k)}, \quad (1)$$

where i,j run over the row and column indexes of an image, respectively; p(i,j,k) and g(i,j,k) denote the predicted probability of the pixel at location (i,j) and the 0/1 ground truth of that pixel belonging to class k, respectively.

Classification Subnet for Fetal/Maternal Side Classification

Because the fetal/maternal side can be inferred from the "disc" region of a placenta alone, we crop the full placenta image x by a rectangle including the region of disc and resize the cropped image to predetermined dimensions (e.g., 512×512 pixels) as the input to the Encoder 310, which we denote as xc. The cropping is based on the ground truth segmentation map during training and on the predicted segmentation map at inference. Our Classification Subnet 350 includes a Res cony block (block 322), two fully connected layers, and a soft-max layer. At the end, a binary cross entropy (BCE) loss is applied to supervise the network at block 324.

IPDecoder for Insertion Point Localization

Because the insertion point is always located within or adjacent to the "disc" region, we use cropped disc region image x, just as we perform cropping in Classification Subnet 350, as the input to the Encoder 310. Our IPDecoder 330 is also fully convolutional and includes two expanding fully convolutional blocks, the structure of which are the same as in the first two convolutional blocks in SegDecoder 340. The similarity of IPDecoder's 330 structure with Seg-Decoder's 340 helps us to ensure that the shared encoder representation could also be readily utilized here. Inspired by the success of intermediate supervision, we predict the insertion point localization heat map after each expanding convolutional block by a convolutional layer with kernel size 1×1 (denoted as "Score block" (block 332 and block 334) in FIG. 3) and use the mean squared error (MSE) loss (block 336 and block 338) to measure the prediction error:

$$L^{ip}=\Sigma_{i,j}\|h(i,j)-\hat{h}(i,j)\|^2, k \in \{1,2\}, \quad (2)$$

where h(i,j) and ĥ(i,j) are the ground truth (Gaussian) heat map and the predicted heat map, respectively. The final loss for insertion point is Lip=Lip+Lip. During inference, the predicted insertion point location is determined by (i,j)=argmaxi,j ĥ(i,j).

Training and Testing

We use mini-batched stochastic gradient descent (SGD) with learning rate 0.1, momentum 0.9, and weight decay 0.0005 for all training. We use a batch size of 2 for all segmentation training and a batch size of 10 for all insertion point localization and fetal/maternal side classification training. The procedures of training are as follows. We first train the SegDecoder 340+Encoder 310 from scratch with parameters initialized to zero. Next, we fix the learned weights for the Encoder 310 and train Classification Subnet 350 and IPDecoder 330 subsequently (in other words, the Encoder only acts as a fixed feature pyramid extractor at this stage). The rationale for making such choices is that the training for segmentation task consumes all images we have gathered and makes use of pixel-wise dense supervision, which is much less likely to lead to an overfitting problem. In contrast, the training for Classification Subnet 350 takes binary value as ground truth for each image while the training for IPDecoder 330 only uses around half of the whole dataset (only fetal-side images). To alleviate the lack of labels and to make the model more robust, we use common augmentation techniques including random rotation (±30°) as well as horizontal and vertical flipping for all training images.

Implementation

We implemented the proposed pipeline in PyTorch and ran experiments on an NVIDIA TITAN Xp GPU. For segmentation training, all images are first resized to 768× 1024, which is of the same aspect ratio as the original placenta images. For insertion point localization and fetal/maternal side classification training, we resize all cropped "disc" region images to 512×512, which is natural because the cropped "disc" regions often have a bounding box close to a square. We summarize all parameter settings for our model in Appendix B.

Stage II: Placenta Feature Analysis

In this stage, we detect pathological indicators based on the results from Stage I.

Detection of Retained Placenta

Retained placenta is a cause of postpartum hemorrhage, and if prolonged, it can serve as a nidus for infection. Trained birth attendants perform a focused examination of the placenta, including inspecting the maternal surface for completeness. However, this process may fail if there is not a trained birth attendant, if blood obscures incomplete areas, or if human error happens. Examination of placentas in pathology also includes assessment of the completeness of the maternal surface, which is recorded in the pathology report. The treatment for retained placenta includes removal of retained parts from the uterus. We identified 119 out of 705 maternal side placenta images in our dataset with possible "retained placenta" based on the pathology reports and we asked a perinatal pathologist to annotate where the possible missing parts are for each of the images. We trained two neural networks for this task, one for classification and one for localization.

The classification network is a binary classification convolutional neural network (CNN) tasked with assessing if the placenta is retained (or incomplete) or not. As the incomplete parts are always within the disk region, the pixels out of the disk region are not considered for the binary classification and were excluded from the input. Thus, we use segmentation maps predicted in Stage I to extract the disk part of a placenta photo by setting pixels not classified as a part of the disc to zeros. Next, we feed the processed placenta photo into the classification network, which is a Resnet-18 network, chosen to suit the small scale of our training set. In training, we fine-tune on our dataset from a model pretrained on ImageNet (with 1,000 classes) using mini-batched stochastic gradient descent (SGD) with batch size 10, learning rate 0.01, momentum 0.9, and weight decay 0.0005 for all experiments.

The localization network assumes that the input placenta image has been classified as retained/incomplete and is tasked with segmenting out the retained/incomplete region(s). We treat it as a two-class segmentation problem and train our localization network, which we choose to be the Deeplab architecture with ResNet-101 as the backbone network (pretrained on ImageNet), against the expert-provided pixel-wise incomplete region labels. Segmentation map predicted in Stage I are used to exclude non-disc regions such that our localization network is not distracted by those pixels. The training set contains 57 images and the testing set contains 12 images. We use SGD with batch size 5, learning rate 0.01, momentum 0.9 and weight decay 0.0005.

Umbilical Cord Insertion Type Categorization

Figure 4:
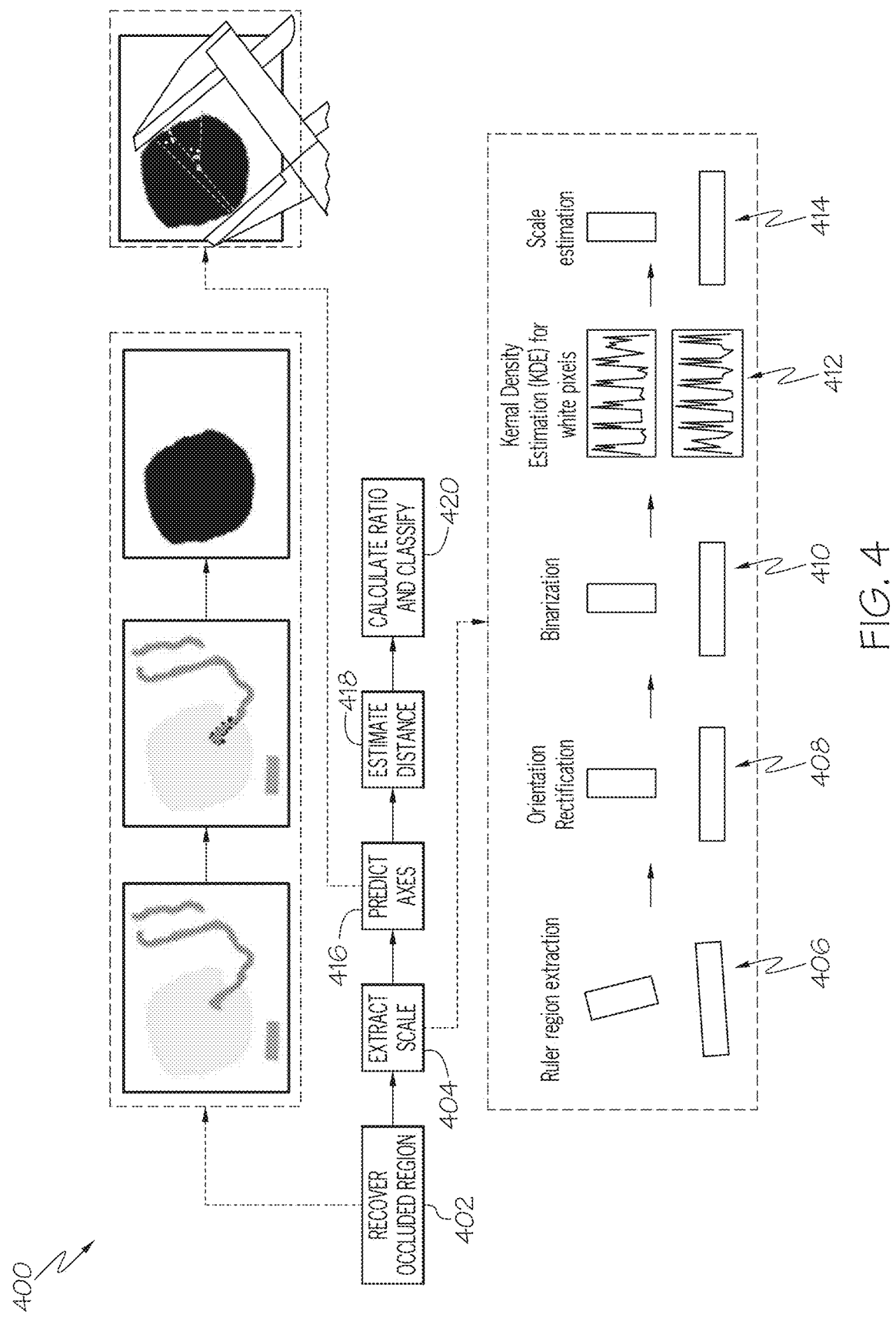
FIG. 4 schematically depicts a flow diagram of an illustrative method of insertion-type categorization and related automated measurements procedures according to one or more embodiments shown and described herein.

Abnormal cord insertion is a feature of fetal vascular mal-perfusion. Based on the segmentation, the predicted insertion point location, and the scale we extracted from the ruler, we can measure the distance from the insertion point to the nearest margin of the disc, the length of the long-axis and short-axis of the disc (all in centimeters). Further, we classify the cord insertion type into "centrally", "eccentrically", and "marginally", based on the ratio of the distance from the insertion point to its closest disc margin to the average length of the long-axis and short-axis. The thresholds for the above ratio between different categories are selected by optimizing classification accuracy on the training set. As illustrated in FIG. 4, the detailed procedures for insertion type categorization and related automated measurements 400 are as follows.

1. We recover the occluded disc area by merging the originally predicted disc area with the polygon defined by vertices adjacent with both disc area and cord area at block 402. Here, erosion and dilation image processing operations are used to remove small holes sometimes appearing in the disc region given by the raw segmentation prediction.
2. We extract the scale information from the ruler at block 404. Since the ruler in the image could be of any orientation, we extract the ruler region at step 406 and rectify the orientation of the ruler and fit a rectangle from the predicted ruler region at step 408. Next, we binarize the pixels within the ruler region at step 410 such that the scale marker is more distinct. Thirdly, we use kernel density estimation to fit a distribution of the marker pixels (white after binarization) along the long edge of the ruler at step 412. Finally, we read the number of pixels corresponding to one centimeter as the number of pixels between the two adjacent crests of the estimated distribution at step 414.

3. We estimate the long-axis and short-axis of a placenta by simulating how pathologists measure those from a 2-D shape by using a vernier caliper at block 416.
4. We estimate the distance from the insertion point to its nearest point on disc margin at block 418.
5. We calculate the ratio of the distance from the insertion point to its closest disc margin to the average length of the long-axis and short-axis and conduct the classification based on pre-selected thresholds based on optimizing training set classification accuracy at block 420.

Meconium, Abruption and Chorioamnionitis Detection

Figure 5A:
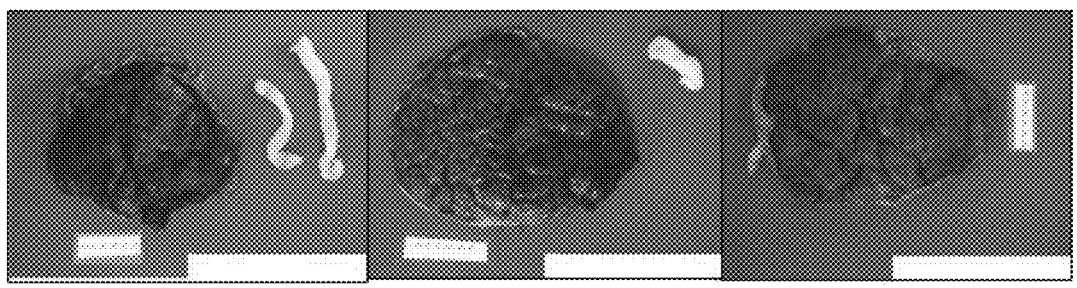
FIG. 5A depicts images of illustrative placental abruption according to one or more embodiments shown and described herein.
Figure 5B:
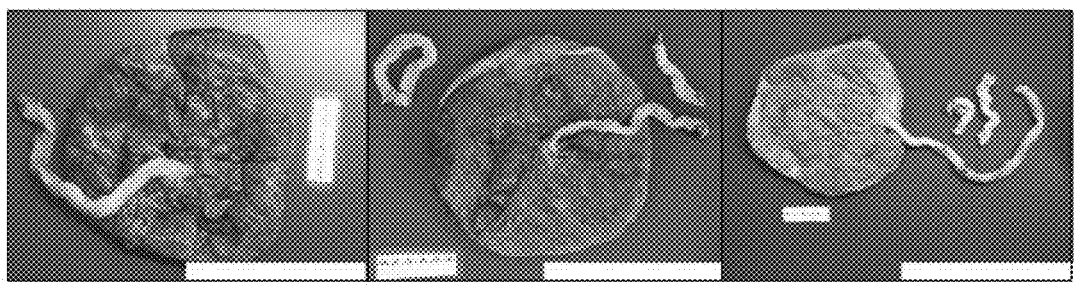
FIG. 5B depicts images of illustrative placental chorioamnionitis according to one or more embodiments shown and described herein.
Figure 5C:
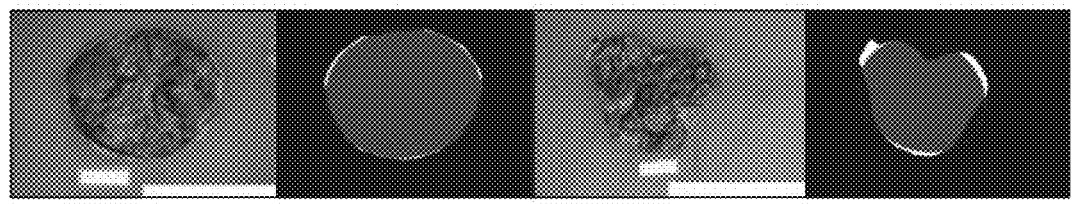
FIG. 5C depicts images of illustrative meconium examples according to one or more embodiments shown and described herein.

Meconium discharge is an indication of fetal distress and can damage the umbilical vessels as well as injure neonatal lungs. Meconium stains on the fetal membranes and/or the fetal surface of the placenta are seen in FIG. 5A. Meconium is not always detectable from the gross color examination as shown in the third image (from left to right) of FIG. 5A and histological analysis is required in some cases. Placental abruption is separation of the placenta from the wall of the uterus before birth and can cause maternal blood loss and fetal distress or death. At delivery, dark red to brown adherent blood clots on the maternal side of placenta may be the main diagnostic characters of abruption; as seen in FIG. 5B, however, this complication is not always visible. Larger clots suggest more severe abruption. Chorioamnionitis is an inflammation of the fetal membranes that often results from bacterial infection and which may progress to devastating infection of the fetus. The fetal surface of the placenta that is affected by chorioamnionitis often looks opaque, with the color ranging from white to yellow to green. The percentage of placenta images diagnosed with meconium, abruption, or chorioamnionitis are relatively low. As a consequence, the number in our fully labeled placenta images are too few for direct training of our model. To address this challenge, we build our training and testing set for these three tasks by using selected images of placentas diagnosed with these three problems out of the 18,400 images we collected in the year of 2016-2018. Specifically, we selected the set of images that satisfied our standards about freshness, non-placenta related objects in the image, etc. In sum, we used 470 meconium diagnosed fetal side images from a total of 731 cases, 268 chorioamnionitis diagnosed fetal side images from a total of 461 cases, and 181 maternal side images with abruption diagnosis from a total of 314 cases. For each task, we build the training and testing set by 1) randomly sampling the same amount of negative cases (not diagnosed with meconium, abruption or chorioamnionitis) as positive cases as found in the whole dataset; 2) splitting the whole assembled dataset into training and testing sets with the ratio of 0.8:0.2.

We trained one simple 6-layer convolutional neural network as the binary classifier for each of the three abnormalities. Only the disc region of an image is fed into those CNN classifiers and non-disc regions of the image are zeroing out based on our segmentation predictions. The first four layers are convolutional layers with filter size of 3, stride of 1, max pooling (for downsampling), relu activation and output sizes are 99×99×32, 48×48×64, 23×23×128, and 10×10×256, respectively. The last two layers are fully connected layers with 1024 neurons and 1 neuron, respectively. At the end, a sigmoid activation is used to scale the output in the range of [0,1] as the probability for each class. We train each network for 30 epochs (until which the training loss has converged) using RMSProp optimizer with learning rate 0.001, momentum 0.9, batch size 10. Since abruption only appears on the maternal side and chorioamnionitis and meconium only appears on the fetal side, our classification network for each of them assumes a placenta image has already been classified into the associated side during inference.

Irregular Shape Detection

Figure 5D:
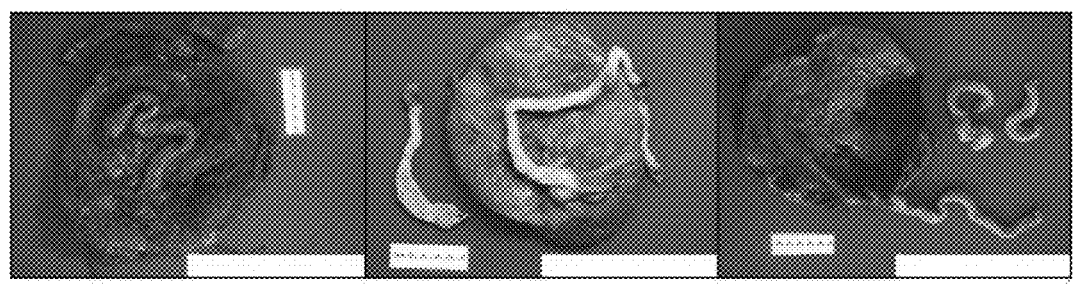
FIG. 5D depicts images of illustrative regular and irregular placental shapes according to one or more embodiments shown and described herein.

Abnormal placental shape has been associated with premature birth or stillbirth. The regular shape for a placenta is round or oval. Meanwhile, those placentas classified as irregularly shaped often looks star-like or calabash-like (as shown in FIG. 5D), with prominent concave or convex parts on the contour of the disc. By imitating how a pathologist determines if the shape of a placenta disc is irregular, we design a simple measure to quantify the irregularity of the disc shape for a placenta. First, we use the same module as in FIG. 4 to recover the occluded disc and produce a whole disc region as a binary map. Next, we find the best-fit ellipse using zeroth-, first-order and second-order moments. The (p+q)-th order moment is defined by:

$$m_{p,q} = \iint x^p y^q f(x,y) dx dy, \tag{3}$$

where $f(x,y)=1$ when the pixel is on the disc area, and zero otherwise. Then we can get the center coordinates $(x_c, y_c)$, the inclination angle $\alpha$ and the long-axis and short-axis a, b of the ellipse following:

$$x_c = \frac{m_{1,0}}{m_{0,0}}, \quad y_c = \frac{m_{0,1}}{m_{0,0}}, \tag{4}$$

$$\alpha = \frac{1}{2}\tan^{-1}\left(\frac{2m_{1,1}}{m_{2,0} - m_{0,2}}\right), \tag{5}$$

$$a = \sqrt{\frac{2}{m_{0,0}}\left(m_{2,0} + m_{0,2} + ((m_{2,0} - m_{0,2})^2 + 4m_{1,1}^2)^{\frac{1}{2}}\right)}, \tag{6}$$

$$b = \sqrt{\frac{2}{m_{0,0}}\left(m_{2,0} + m_{0,2} - ((m_{2,0} - m_{0,2})^2 + 4m_{1,1}^2)^{\frac{1}{2}}\right)}, \tag{7}$$

Finally, we count the number of pixels covered by the fitted ellipse (denoted as n1), the number of disc pixels outside the fitted ellipse (denoted as n2), and the number of non-disc pixels within the ellipse (denoted as n3, those pixels are white ones in FIGS. 5A-5E). We also define $$I = \frac{n_2 + n_1}{n_1}, \tag{8}$$

as the measure of irregularity for disc shape. Obviously, the larger the I, the more irregular a disc shape is. We select a threshold for I from the training set such that we classify a placenta as irregular-shaped if its I is larger than that threshold. Two examples of regular and irregular shaped placentas, along with their disc binary maps and fitted ellipses are displayed in FIG. 5D.

Hypercoiled Cord Identification

Figure 6A:
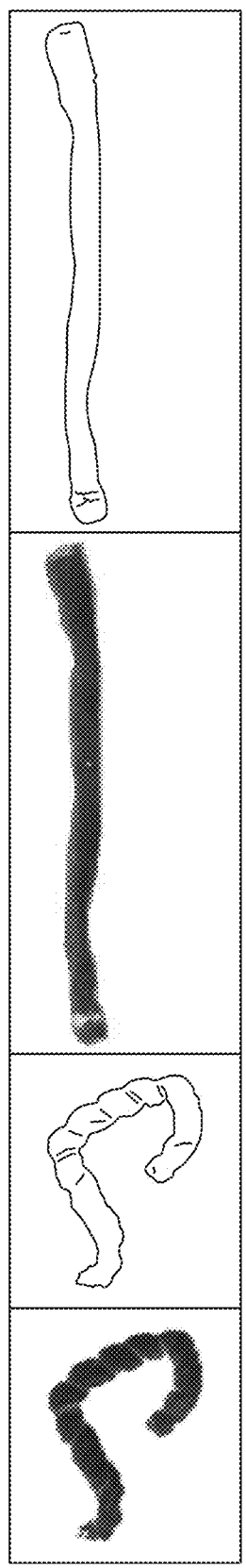
FIG. 6A depicts images of an illustrative hypercoiled cord and a normal cord according to one or more embodiments shown and described herein.
Figure 6B:
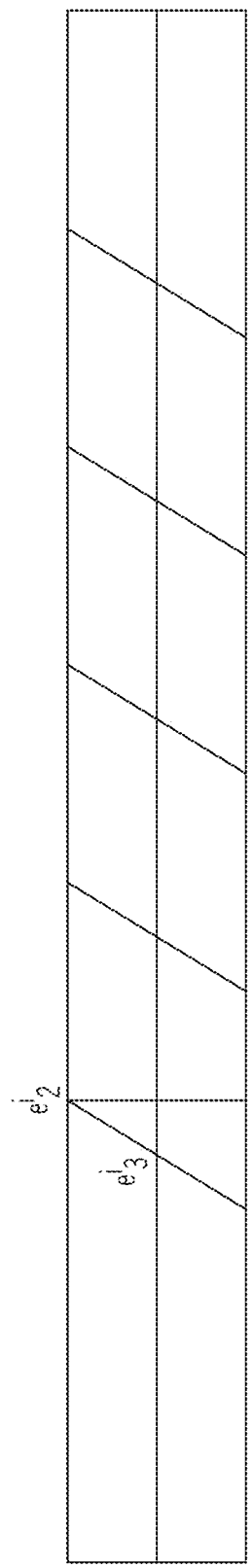
FIG. 6B schematically depicts coil counting from an extracted edge from the images depicted in FIG. 6A according to one or more embodiments shown and described herein.

As illustrated in FIG. 6A, a hypercoiled cord is more twisted than a normal cord, impairing fetal blood flow. Detecting this phenomenon is important because it is linked to infant mortality. Our approach is to apply Canny edge detection on the cord region predicted by our segmentation model to detect fold crevices caused by hypercoiling. The count of those fold crevices could be a good approximation to the actual number of coils because it is also the main clue for pathologists to identify an individual coil and count the total number of coils using bare eyes. Before counting, we disregarded the detected fold crevices that are very small (in terms of length), crossed with the adjacent one, or whose orientation is too parallel with the orientation of the central skeleton of the cord. FIG. 6A shows two examples of our intermediate results for fold crevices detection. Sometimes, there are two or more edge segments extracted for one crevice, which will result in incorrect count of coils if we blindly count the number of extracted edge segments. We design a simple but effective rule, as illustrated in FIG. 6B, to overcome this:

Let $e_1^i$, $e_2^i$ and $e_3^i$ be the points of intersection between the i-th segment and the two cord boundaries and the central skeleton, respectively. Let $e_4$ be $e_2$'s projection (in the direction vertical to the central skeleton) onto the opposite boundary.

Denote the length of the boundary between $e_1^i$ and $e_4^i$ as $T_i$. Denote the distance between $e_1^k$ ($k \geq i+1$) of the k-th segment and $e_1^i$ be $d^{ik}$.

If $d^{ik} > 2T_i$, then the k-th segment will be counted as a coil. Otherwise, the k-th segment will not be counted.

Let's denote n the count of coils we obtain following the above rule and l the cord length in centimeters. We can quantify the coilness of a cord by:

$$C = \frac{n \times 10}{l} \quad (9)$$

e.g., the number of coils per ten centimeters. After exploring the hypercoiled cords in the training set, we define a cord to be "hypercoiled" if $C \geq 4$, which leads to the best training set accuracy when it is used as the classification criterion.

Knot Detection

Figure 5E:
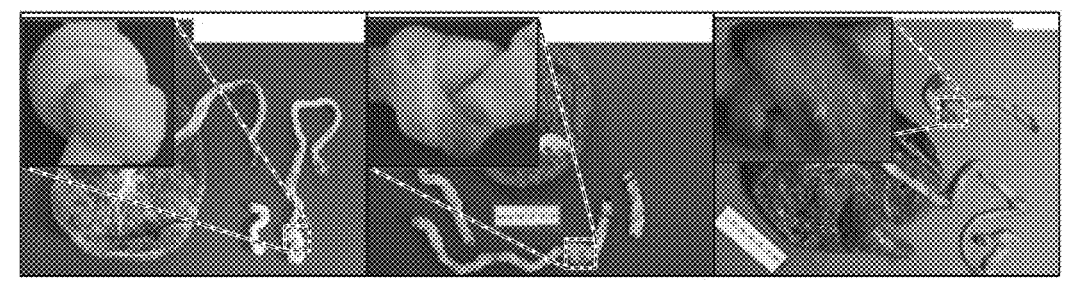
FIG. 5E depicts images of illustrative true knots on the umbilical cord according to one or more embodiments shown and described herein.

A true knot forms when the umbilical cord ties around itself. FIG. 5E shows some examples of true knots. Loosely looped knots do not usually present a problem, while tight knots can severely affect the blood and oxygen exchange between the mother and the fetus. Therefore, knot detection is included as a routine examination by clinical staff at delivery and in the gross pathological exam. In a regular pathology report, a placenta is diagnosed with "normal" or "having true knots" or "having false knots" (which means the image does not contain true knot(s) but some part(s) of cords are very similar to true knots), In our dataset, we have 171 images diagnosed with having true knots and 462 images diagnosed with having false knots. For each placenta image diagnosed with having true knots, we manually labelled all the true knots with bounding boxes. Using these labeled images, we trained our knots detection module from scratch. For the knot detection task, we use YOLO, a single-stage detection network. We used the original RGB image concatenated with a binary mask denoting the cord region predicted by our segmentation as the input to the detection network and trained our detection network against the expert-labeled bounding boxes. As before, we used the 0.8:0.2 ratio to split the original dataset into training and testing sets. We used batch size 64 and learning rate 0.001.

RESULTS

In this section, we summarize the experimental results using our dataset. The results are organized by the two stages and then by the individual tasks within each stage. We also discuss the inference time and the clinical significance at the end of this section.

Morphological Characterization

Segmentation

We compared our approach with two fully convolutional encoder-decoder architectures, the U-Net (Ronneberger et al., 2015) and the SegNet (Badrinarayanan et al., 2017). The results are shown in Table 1 below and FIGS. 7A-7D.

TABLE 1

Segmentation evaluation

| Model | pixel acc. | class acc. | mean IoU |
| --- | --- | --- | --- |
| U-Net | 98.10 | 92.98 | 88.21 |
| SegNet | 96.51 | 94.56 | 84.57 |
| ours | 98.73 | 97.26 | 93.93 |

We report the segmentation performance using standard segmentation metrics pixel accuracy, mean accuracy, and mean IoU. The definition of those metrics are as follows: suppose we have counted how many pixels are predicted to class j but with their ground truth being class i (for every $i, j \in \{0, 1, \ldots, k-1\}$, k is the number of classes) and we store it as the term $C_{i,j}$ in a k×k matrix C. We also denote the (ground truth) total number of pixels for class i as $T_i$. It is easy to see that $T_i = \sum_{j=0}^{k-1} C_{i,j}$. The pixel accuracy, mean class accuracy, and mean IoU are then defined as follows.

Pixel Accuracy:

$$\frac{\sum_{i=0}^{k-1} C_{i,j}}{\sum_{i=0}^{k-1} T_i} \quad (10)$$

Mean Class Accuracy:

$$\frac{1}{k} \frac{\sum_{i=0}^{k-1} C_{i,j}}{T_i} \quad (11)$$

Mean IoU:

$$\frac{1}{k} \sum_{i=0}^{k-1} \frac{C_{i,j}}{T_i + \sum_{j \neq i} C_{i,j}} \quad (12)$$

Figure 7B:
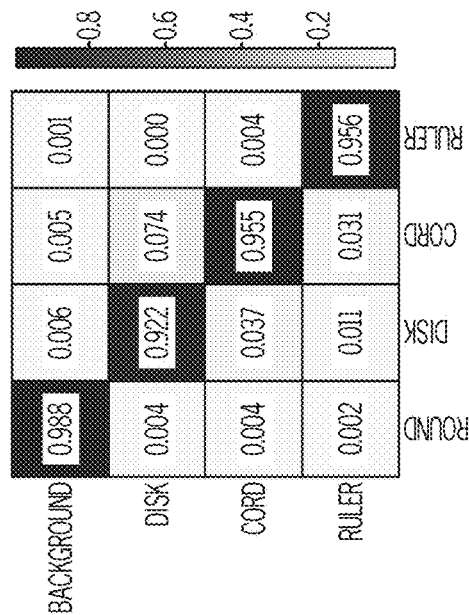
FIG. 7B depicts a pixel-wise prediction confusion matrix of a U-Net approach.
Figure 7C:
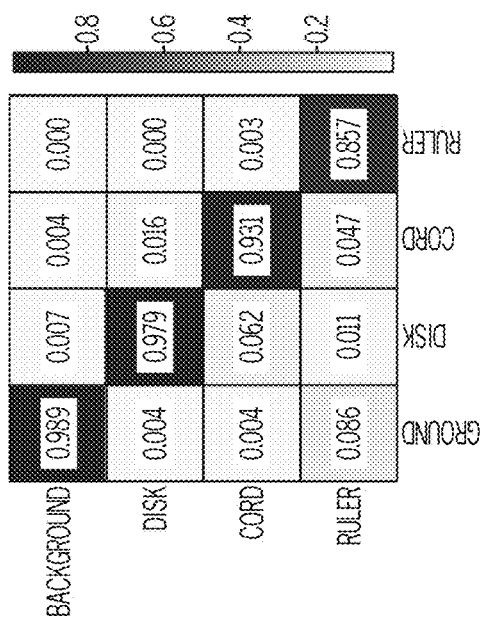
FIG. 7C depicts a pixel-wise prediction confusion matrix of a Segnet approach.
Figure 7A:
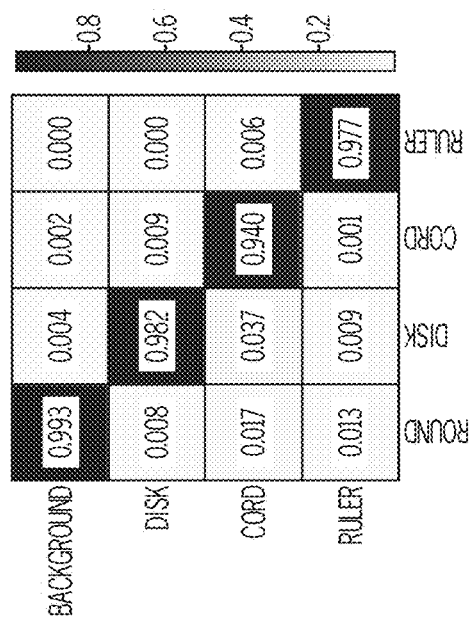
FIG. 7A depicts a pixel-wise prediction confusion matrix according to one or more embodiments shown and described herein.
Figure 7D:
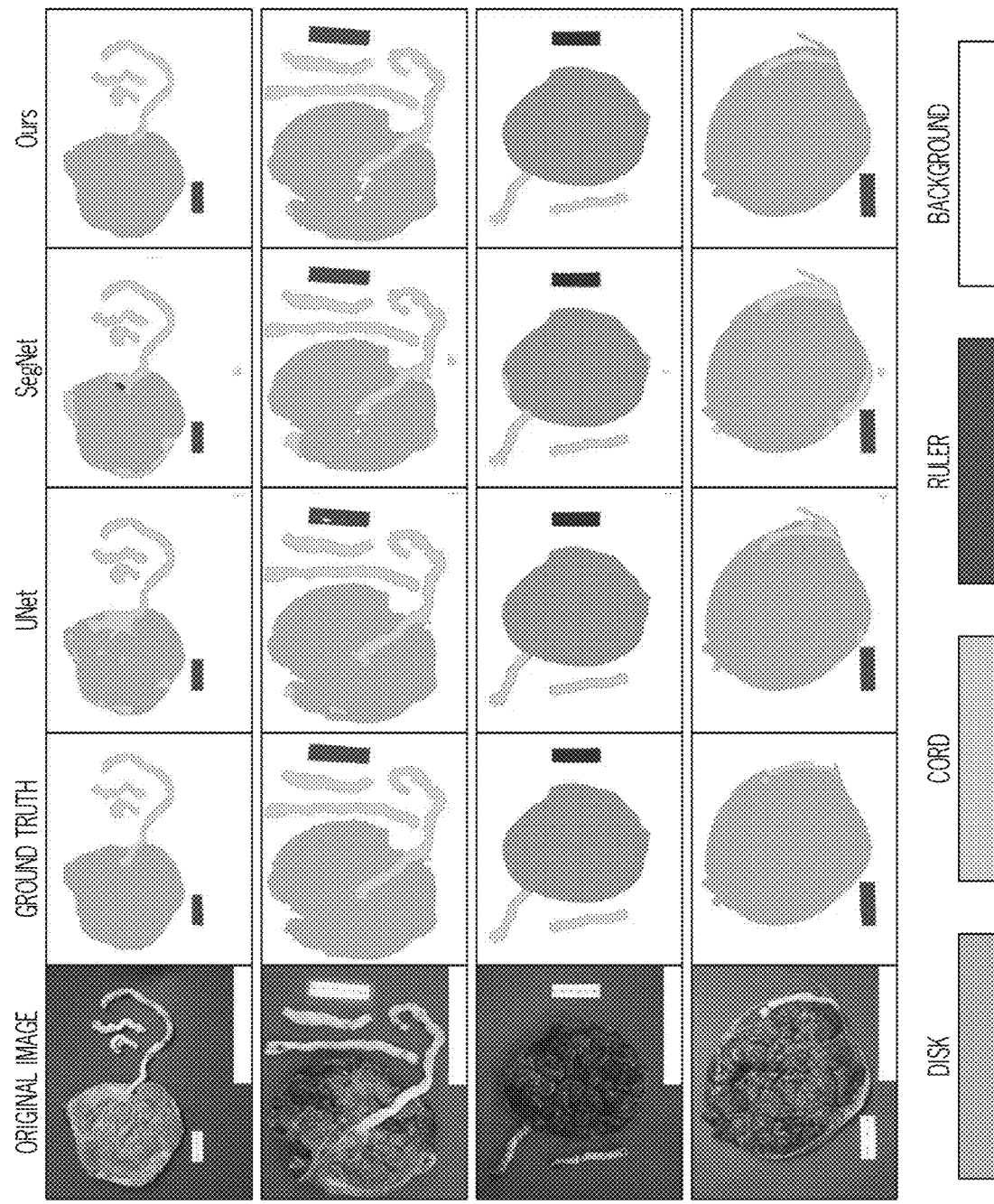
FIG. 7D depicts images of illustrative examples of segmentation approaches according to one or more embodiments shown and described herein.

In FIGS. 7A-7C, we compare pixel-wise prediction confusion matrices of our approach, U-Net, and Segnet, respectively, which reflects more details about segmentation performance for different categories. We also show a few segmentation examples in FIG. 7D for qualitative comparison. Our approach yields the best segmentation results, especially for differentiating the cord and the ruler classes.

Fetal/Maternal Side Classification

Figure 8A:
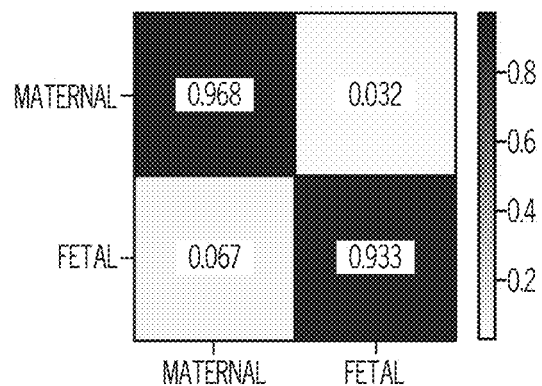
FIG. 8A depicts a fetal/maternal-side classification confusion matrix without shared encoder weights according to one or more embodiments shown and described herein.
Figure 8B:
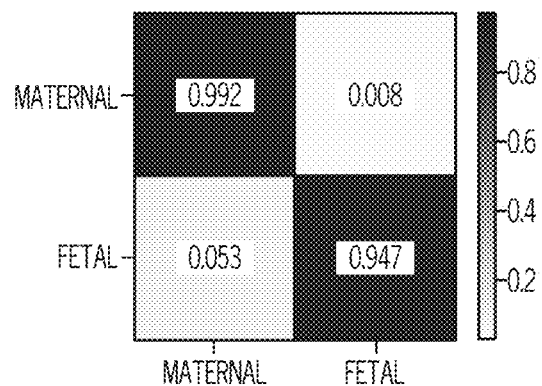
FIG. 8B depicts a fetal/maternal-side classification confusion matrix with shared encoder weights according to one or more embodiments shown and described herein.

We achieved an overall fetal/maternal side classification accuracy of 97.51% on our test set. Without the shared encoder representation, we can only achieve 95.52% by training Encoder+Classification Subnet from scratch. We also compare their confusion matrices in FIGS. 8A-8B.

Insertion Point Localization

Figure 9A:
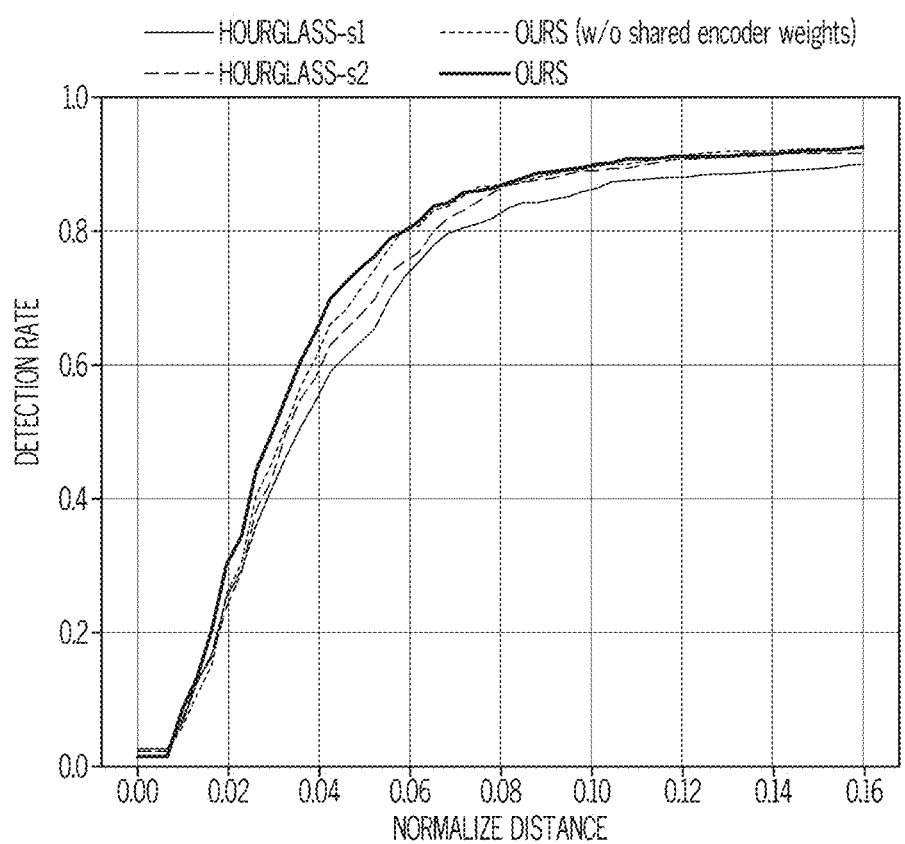
FIG. 9A depicts a plot of a quantitative evaluation of insertion point localization with a percentage of correct keypoints according to one or more embodiments shown and described herein.
Figure 9B:
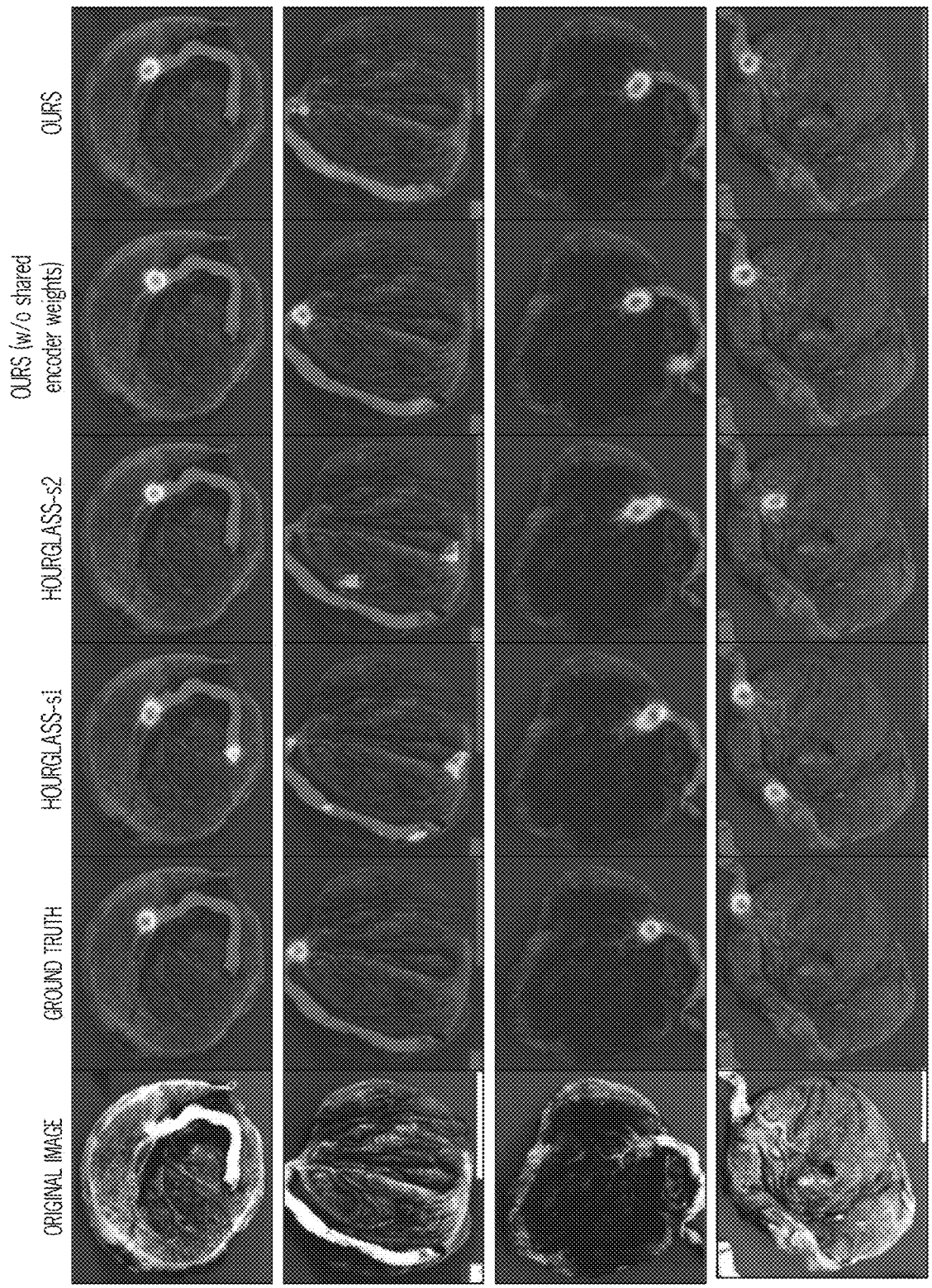
FIG. 9B depicts images of qualitative examples of insertion point heat map predictions according to one or more embodiments shown and described herein.

We choose Percentage of Correct Keypoints (PCK) as the evaluation metric. PCK measures the percentage of the predictions fall within a circle of certain radius centered at the ground truth location. More formally, PCK at normalized distance x ($x \in [0, 1]$) is defined as:

$$PCK@x = \frac{\left| p: \frac{\sqrt{\|\hat{p} - p\|_2}}{d} < x \bigwedge p \in \{p_i\}_{i=1}^n \right|}{n}, \quad (13)$$

where $\{p_i\}_{i=1}^n$ are the n keypoints we are trying to predict. $\hat{p}$ stands for our prediction for p; $\|\bullet\|_2$ stands for the L-2 Euclidean distance and is used to measure the error of the prediction $\hat{p}$ from the ground truth p; $|\bullet|$ stands for the cardinality of a set. Herein, we choose the diameter of the disc as the normalizing factor d. In practice, we approximate the diameter of the disc by the distance between the right most and left most pixel of the "disc" area in the segmentation map. In comparing our approach (both with and without shared encoder weights) to the Hourglass model (with number of stacks 1 and 2), we see competitive results achieved by our approach in human keypoint localization. FIG. 9A shows the PCK curves, with the x axis being the radius normalized by the diameter of the placenta. Each curve in FIG. 9A is the average of the results for five models trained with different seeds, and the light-colored band around each curve (view-able when the figure is enlarged) shows the standard deviation of the results. Our approach with shared Encoder 310 (FIG. 3) consistently gives the best results, especially when the normalized distance is from 0.2 to 0.6. We also show a few qualitative examples of the insertion point heat maps predicted by each model, along with the ground truth in FIG. 9B.

Placenta Feature Analysis

The predictions of the Stage I models enable us to conduct automatic placenta feature analysis by subsequent models/procedures.

Detection of Retained Placenta

Figure 10A:
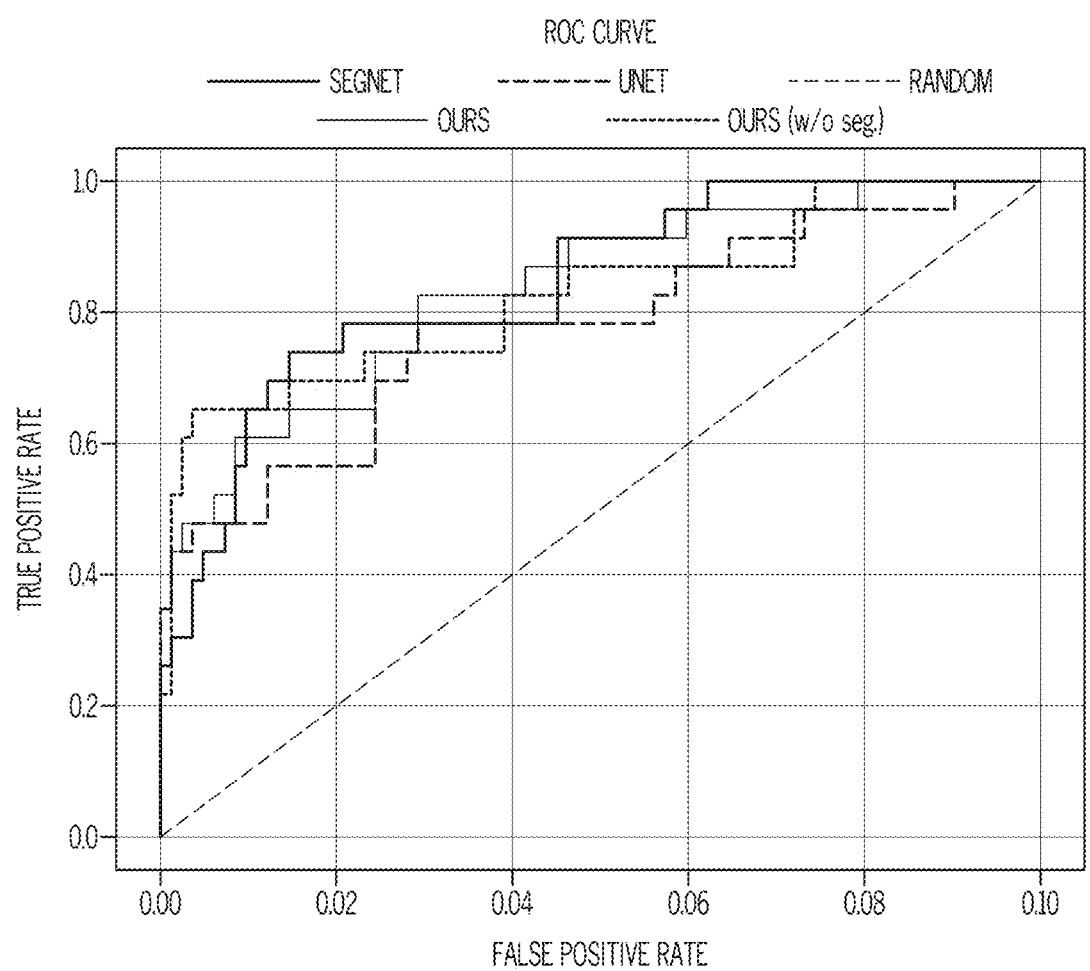
FIG. 10A depicts a plot of a receiver operating characteristic (ROC) curve for a classification network according to one or more embodiments shown and described herein.
Figure 10B:
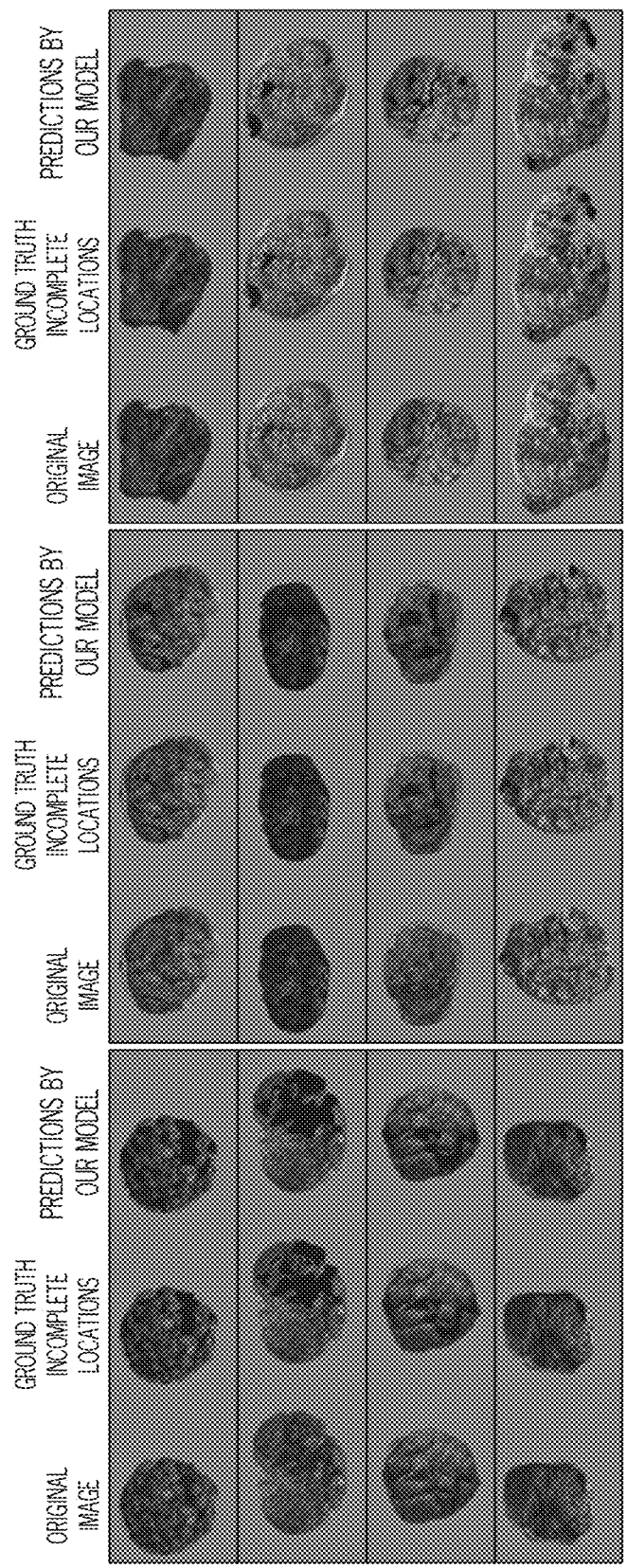
FIG. 10B depicts images of qualitative examples of incomplete part localization predictions produced by a localization network according to one or more embodiments shown and described herein.

Both our classification network and localization network achieve promising results. We show the receiver operating characteristic curve of the classification network in FIG. 10A and example localization results along with the ground truth in FIG. 10B. To show the advantage of using the disc region only as the input, we compare two versions of classification network in FIG. 10A, one with segmented disc region only (with AUC 0.836) and one without using our segmentation predictions (with AUC 0.827). We also show the results of our classification network based on the disc regions provided by UNet (with AUC 0.781) and SegNet (with AUC 0.844) segmentation. The results based on our segmentation network in Stage-I is significantly better than the results based on UNet, and on par with or slightly worse than the results based on SegNet. We have expanded our pool of images with expert-labeled incomplete region (around 2x) and improved our localization results from IOU=0.571 to IOU=0.636 by training on this expanded pool of labeled images. This improvement is also significant in our qualitative examples shown in FIG. 10A.

Umbilical Cord Insertion Type Categorization

Figure 11C:
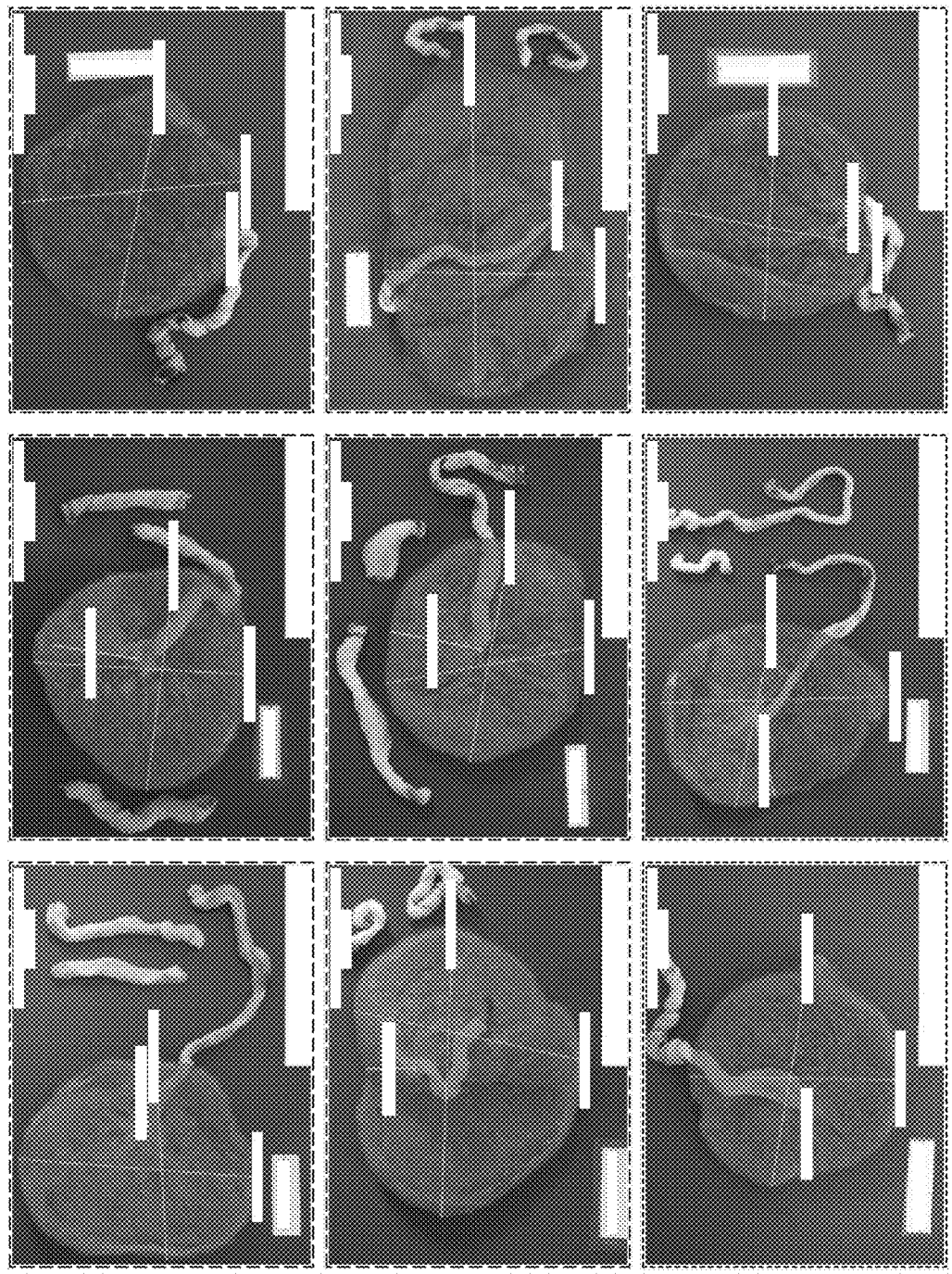
FIG. 11C depicts images of qualitative examples of insertion point type categorization according to one or more embodiments shown and described herein.

We achieved an overall 88% test accuracy and we show the classification confusion matrix in FIG. 11A. Because the ground truth distance from the insertion point to its nearest point on the disc margin can be extracted from the pathology reports, as shown in Appendix A, we are able to evaluate our prediction for this important intermediate value. FIG. 11B shows the evaluation for our estimation of the distance from the insertion point to its nearest point on the disc margin on the test set. The x-axis represents the threshold of the normalized error (absolute error normalized by the ground truth) and the y-axis shows the percentage of our estimation, the error of which is below such threshold. As shown, we have a 58% prediction accuracy if we set the threshold to 0.2. Qualitative examples of our insertion type categorization and associated automated categorization can be found in FIG. 11C. Insertion type predictions are displayed in the upper right corner of each image, along with the ground truth in brackets. The success cases are green boxed and the failed cases are red boxed. For each image, the predicted insertion point locations are marked with a green dot; a transparent green mask is overlaid on the image representing the predicted whole disc region; a line is drawn between the insertion point and its nearest point on the disc margin. The predicted length of such line is displayed next to it, along with the ground truth length extracted from the pathology report (in brackets). The predicted long and short axes are also displayed, along with their predicted length in centimeters. We can see that the results for both the umbilical cord insertion type categorization and its related measurements are very appealing. Our method is already very promising as a replacement for the current approach based on the manual measurement and naked-eye inspection.

Meconium, Abruption, and Chorioamnionitis Detection

Figure 12A:
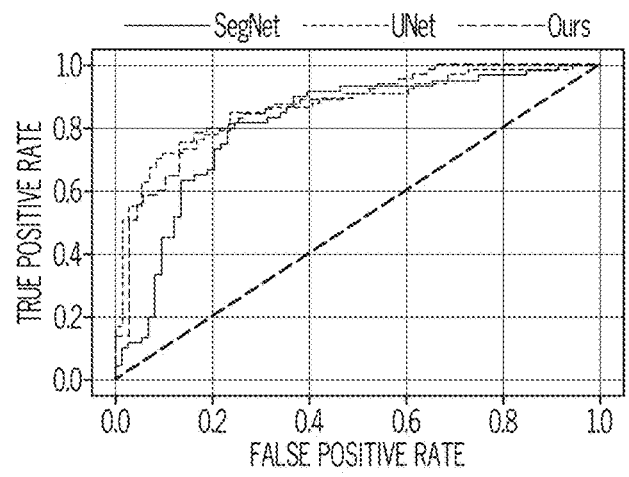
FIG. 12A depicts a plot of illustrative receiver operating characteristic curves for detecting meconium according to one or more embodiments shown and described herein.
Figure 12B:
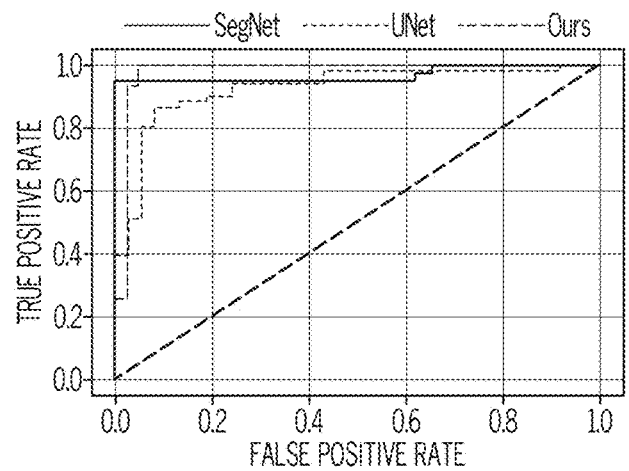
FIG. 12B depicts a plot of illustrative receiver operating characteristic curves for detecting abruption according to one or more embodiments shown and described herein.
Figure 12C:
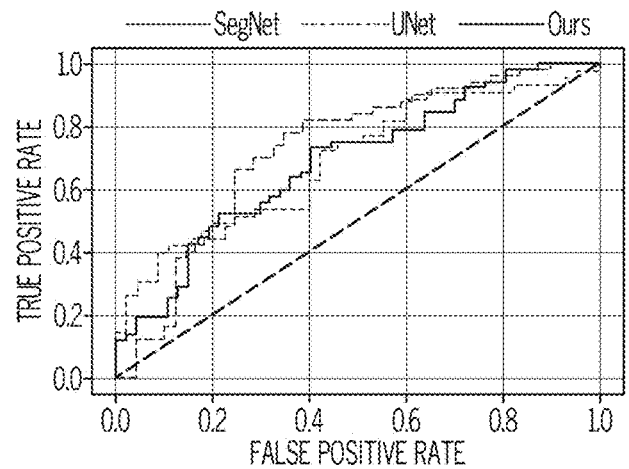
FIG. 12C depicts a plot of illustrative receiver operating characteristic curves for detecting chorioamnionitis according to one or more embodiments shown and described herein.

The receiver operating characteristic (ROC) curves of binary classifiers for meconium, abruption, and chorioamnionitis are shown in FIGS. 12A, 12B, and 12C, respectively. We achieved 0.97/0.98, 0.72/0.72 and 0.70/0.69 in terms of sensitivity and specificity for the detection of abruption, meconium, and chorioamnionitis, respectively, under the selected operating point marked on the ROC curve as shown in FIGS. 12A-12C. We also show ROC curves of binary classifiers for meconium, abruption, and chorioamnionitis based on UNet and SegNet segmentations in each sub-figure. Overall, our segmentation network described in Stage-I is the best choice to achieve the best ROC curve for all three tasks.

Irregular Shape Detection

In our dataset, 77 placentas are labeled as irregular shaped. By maximizing training set accuracy, we chose 0.14 as the irregularity measure (Eq. 8) threshold for classifying the shape. The sensitivity and specificity for shape classification are 0.87 and 0.97, respectively, using the selected threshold. On expert review, the shape labels in pathology report are quite subjective, which we believe is the main limiting factor for achieving better classification performance in our model. We can, however, make the shape classification much more objective by switching from the current naked-eye inspection approach to our computer-based approach.

Hypercoiled Cord Identification

Our dataset contains a total of 143 cords that are labeled as hypercoiled. The sensitivity and specificity for cord classification are 0.85 and 0.93, respectively, under the selected coilness threshold. We believe the results still have room for improvement. The main factors hindering our method from achieving better accuracy include blood stains within the image, faint edges on the cord, limited number of hypercoiled cases for selecting the threshold, and the cord segmentation prediction error.

Knot Detection

Figure 13A:
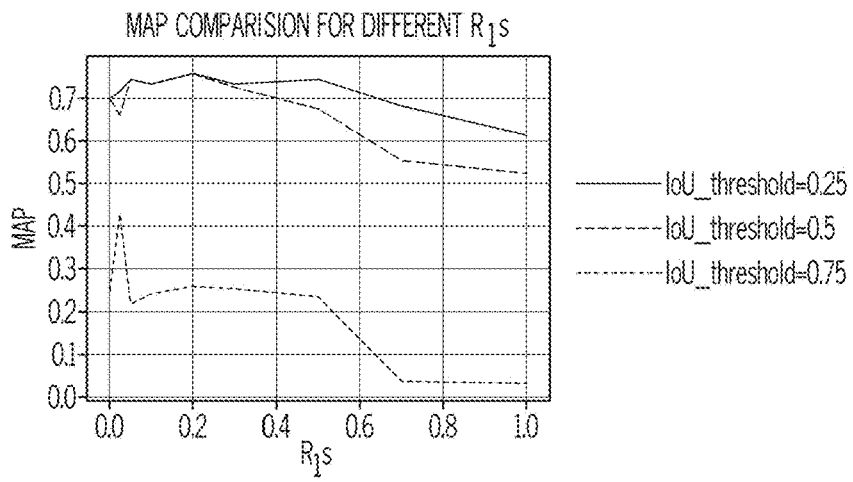
FIG. 13A depicts a plot of a comparison of mean average accuracy (MAP) between different ratios of the probability to sample an image with false knot or no knot over the probability to sample an image with true knot (41) under IoU threshold 0.25, 0.5, and 0.75 according to one or more embodiments shown and described herein.
Figure 13B:
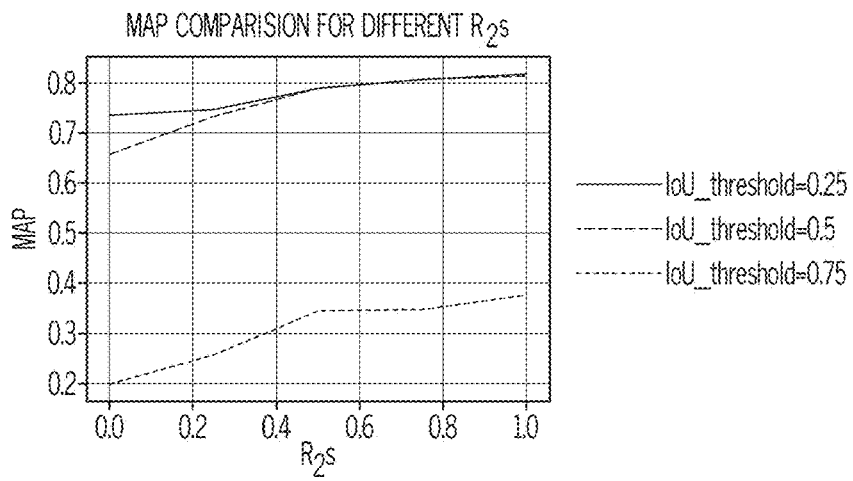
FIG. 13B depicts a plot of a comparison of mean average accuracy (MAP) between different ratios of the probability to sample an image with false knot over the probability to sample an image with no knot (R2) under IoU threshold 0.25, 0.5, and 0.75, assuming R1=2 (the best from the results of FIG. 13A) according to one or more embodiments shown and described herein.
Figure 13C:
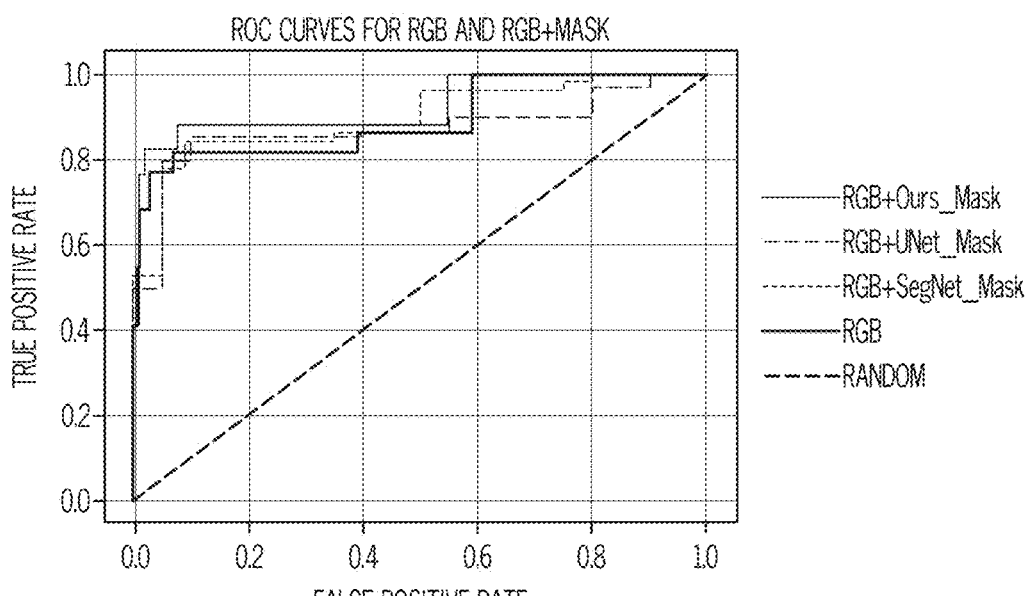
FIG. 13C depicts a plot of a comparison of receiver operating characteristic (ROC) curves between using RGB only vs. RGB+MASK as an input at IoU threshold 0.5 according to one or more embodiments shown and described herein.
Figure 13D:
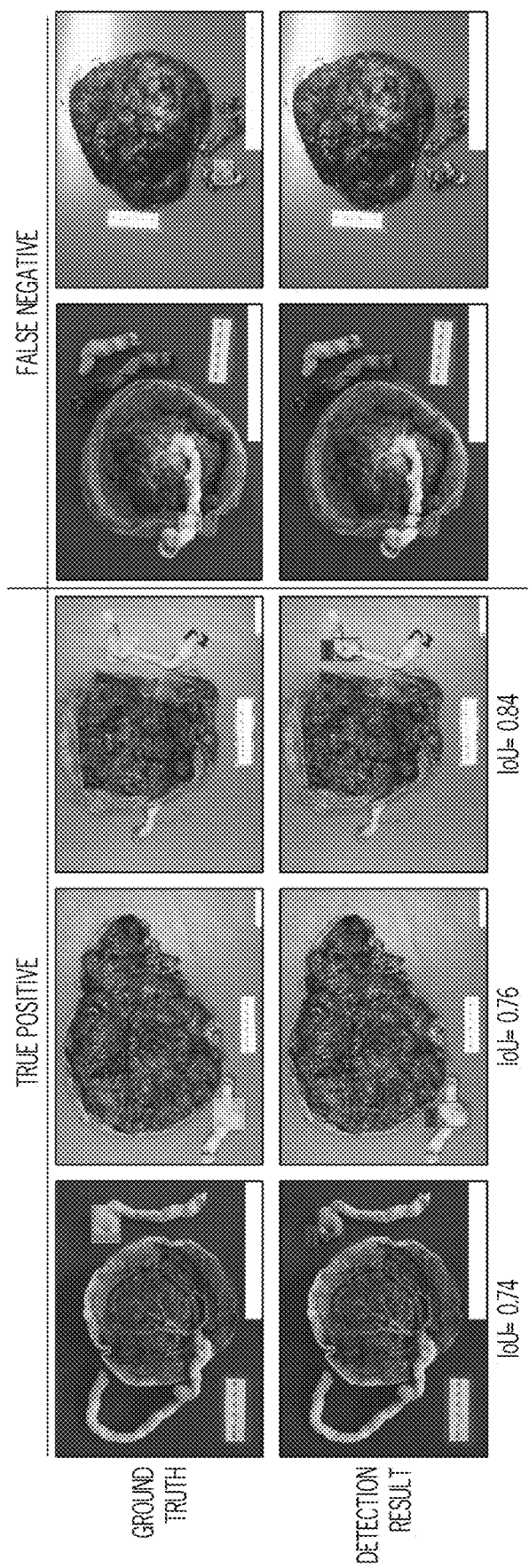
FIG. 13D depicts images of example detection results using RGB+MASK as input and R1=2 and R2=1.0 with IoU values also indicated for each example according to one or more embodiments shown and described herein.

We used the standard metric, mean average precision (MAP) under different thresholds of intersection over union (IoU) to evaluate our detection performance. In our dataset, the number of positive examples is significantly less than the number of negative examples and the number of hard negative examples (false knot) is significantly less than the number of easy negative examples (no knot). Such imbalance of different classes and imbalance of easy cases and hard cases could hurt the model's performance due to the dominating influence on the loss from the class in majority (or from the easy cases). This phenomenon has been verified and studied in many other applications and models. To address such a problem, we must balance the influence of different classes (or easy/hard cases) on the loss, either through an explicit re-weighting scheme by multiplying a scalar or implicit re-weighting scheme by adjusting the sampling for SGD. In that regard, we explored different sampling strategies instead of the default uniform sampling strategy when we use SGD to train our detection network. We present the results in FIGS. 13A and 13B. Specifically, we swept the ratio of the probability of sampling an image with a false knot or no knot over the probability of sampling an image with a true knot (R1) and the ratio of the probability of sampling an image with a false knot over the probability of sampling an image with no knot (R2). We then compare detection performance on the same test set under the training settings with different R1 (FIG. 13A) and different R2 (FIG. 13B). By default, if we sample uniformly from the training set, disregarding if a sample is positive/negative or is a easy/hard case, R1=7 and R2=0.5. We can see from FIG. 13A and FIG. 13B that we can achieve significantly better performance by decreasing R2 and increasing R1 from the default value, which translates to forcing our model attend more to negative cases (false knot or no knot), especially the hard negative cases (false knot). Under the best setting we selected (R1=2 and R2=1.0), we can achieve MAP 0.817, 0.813, 0.376 for IoU thresholds of 0.25, 0.5, and 0.75, respectively. Given the detection results by our model, we are able to classify whether an image has a true knot. And since classification itself is important in practice, we also show the ROC curve for our model from a binary classification perspective in FIG. 13C. As before, by concatenating the binary mask (given by our segmentation model in stage 1) for the cord with the original image's RGB channels, we achieve significant additional performance improvement. Quantitatively, we improved MAP from 0.77 to 0.81 and ROC curve from the blue line (AUC=0.89) to the orange line (AUC=0.93) in FIG. 13(c) by switching from RGB only to RGB+Ours Mask as the input. Besides, when we concatenate the segmented masks provided by UNet and SegNet instead of the segmentation network in Stage-I, the ROC curves become worse, and their AUC drop to 0.87 and 0.90, respectively. This again demonstrates the superior performance of our segmentation method. A few qualitative examples of true knot detection (our best model with R1=2 and R2=1.0 and using RGB+Ours MASK as input) are shown in FIG. 13D.

Inference Time and Discussion on the Clinical Significance

Inference Time

Table 2 below summarizes the inference time of each individual component of our approach. For components not involving neural networks, we estimate the computation time by averaging over 10 images; for components involving neural networks accelerated by GPU, we estimate the computation time by averaging the inference time for 20 batches of images. Inference batch size used for each component is also displayed in Table 2. If we conduct segmentation for the maternal and fetal images at the same time and all other steps sequentially, the total inference time for a placenta is about 3.26 second. Moreover, if we parallelize the computation of Side classification and Insertion point estimation in Stage-I and all parallelizable components in Stage-II, the total inference time for a placenta is about 1.58 second. The inference time of the bottleneck components for the total inference time estimation are underlined in Table 2.

TABLE 2

Summary of inference time

| Component | Inference time (s./img.) | Batch size |
|---|---|---|
| Segmentation | 0.53 | 2 |
| Side classification | 0.09 | 10 |
| Insertion point estimation | 0.18 | 10 |
| Retained placenta classification | 0.11 | 32 |
| Retained placenta localization | 0.47 | 10 |
| Insertion type categorization | 0.87 | NA |
| Meconium detection | 0.19 | 16 |
| Abruption detection | 0.23 | 16 |
| Chorioamnionitis detection | 0.19 | 16 |
| Irregular shape detection | 0.39 | NA |
| Hypercoiled cord identification | 0.31 | NA |
| Knot detection | 0.28 | 10 |

Discussion on Clinical Significance

Our approach can significantly reduce the work burden of clinicians. Currently it takes about 15 minutes for a trained physician at Northwestern Memorial Hospital to examine the placenta and produce a pathology report that covers all diagnoses tackled by our approach, according to the perinatal pathologist (coauthor) in our team. This is about 276 (569) times of the inference time of the sequential (parallel) version of our approach. More importantly, the benefits of a fully automatic system are not limited to faster inference time. Other benefits of our approach include:

High objectivity: There can be inconsistent diagnoses among a group of physicians or even with the same physician over time. Our approach, however, always predicts using the same set of criteria and is a deterministic process.

24/7 availability and flexibility: For instance, if a woman delivers on Saturday at noon, the placenta won't even make it to the pathology lab until the next Monday morning. In contrast, our approach can provide timely on-site diagnoses so prompt treatment can be given to the mother and/or the baby if necessary.

Scalability: By deploying our system in cloud services, we can use more machines when the demand is high. In contrast, it's costly to train and employ pathologists to meet sudden higher demand of the service.

We proposed a two-stage pipeline to address the tasks for automated placental assessment and examination. In the first stage, we designed a compact multi-head encoder-decoder CNN to jointly solve morphological placental characterization tasks by employing a transfer learning training strategy. We showed that our approach can achieve better performance than competitive baselines for each task. We also showed that the representation learned from the segmentation task can benefit insertion point localization and fetal/maternal side classification task. In the second stage, we used the output from the first stage, as well as the original placenta photos, as the input and employed multiple independent models for a few noteworthy placental assessment tasks. Through ablation experiments, we demonstrated that the predictions from the first stage models help us achieve better performance for tasks in this stage. For second-stage placenta feature analysis tasks, though our results still have room to be improved, especially when more placental images diagnosed with those abnormalities are available in the future, our current approaches are already useful for triage purpose, which could significantly alleviate the workload for pathologists.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A system for completing a morphological characterization of a digital image of a placenta, the system comprising:
   one or more processing devices; and
   one or more non-transitory, processor-readable storage mediums having programming instructions thereon that, when executed, cause the one or more processing devices to execute commands according to the following logic modules:
      an Encoder module that receives the digital image of the placenta and outputs a pyramid of feature maps;
      a SegDecoder module that segments the pyramid of feature maps on a fetal side image and on a maternal side image;
      a Classification Subnet module that classifies the fetal side image and the maternal side image; and
      a convolutional IPDecoder module that localizes an umbilical cord insertion point of the placenta from the classified fetal side image and the classified maternal side image,
      wherein the localized umbilical cord insertion point, a segmentation map for the classified fetal side image, and a segmentation map for the classified maternal side image are provided to an external device for the purposes of determining the morphological characterization by the external device.

2. The system of claim 1, wherein the SegDecoder module includes a plurality of expanding fully convolutional blocks, wherein each of the plurality of expanding fully convolutional blocks transposes a convoluted output feature map of a last layer of a concatenation of a copy of the feature maps and applies soft-max to predict a probability of a pixel being of a particular class.

3. The system of claim 2, wherein the SegDecoder module solves the following equation:

$$L^{seg} = 1 - \frac{\sum_{i,j}\sum_{k=0}^{3} p(i,j,k) \cdot g(i,j,k)}{\sum_{i,j}\sum_{k=0}^{3} p^2(i,j,k) + g^2(i,j,k)},$$

where i,j are coordinates of a location of the pixel, p(i,j,k) and g(i,j,k) denote a predicted probability of the pixel at the location (i,j) and a 0/1 ground truth of the pixel belonging to class k, respectively.

4. The system of claim 1, wherein the digital image received by the Encoder module is a full placenta image that is cropped to a region including a disc portion of the placenta and resized to predetermined dimensions.

5. The system of claim 1, wherein the IPDecoder module comprises a plurality of expanding fully convolutional blocks.

6. The system of claim 5, wherein the IPDecoder module is configured to predict the insertion point as a localization heat map after each expanding convolutional block of the plurality of expanding fully convolutional blocks by a convolutional layer having a kernel size and using a mean squared error loss to measure a prediction error:

$$L^{ip} = \Sigma_{i,j}\|h(i,j) - \hat{h}(i,j)\|^2, k \in \{1,2\},$$

where h(i,j) and $\hat{h}$(i,j) are the ground truth (Gaussian) heat map and the predicted heat map, respectively.

7. The system of claim 1, further comprising an imaging device communicatively coupled to the one or more processing devices, the imaging device capturing the digital image of the placenta.

8. The system of claim 1, further comprising an image repository communicatively coupled to the one or more processing devices, the image repository storing the digital image of the placenta.

9. The system of claim 1, wherein the morphological characterization provides the external device with an ability to predict a pathological diagnosis of the placenta, the pathological diagnosis selected from one or more of a retained placenta classification diagnosis, a retained placenta localization diagnosis, an insertion type categorization diagnosis, a meconium detection diagnosis, an abruption detection diagnosis, a chorioamnionitis detection diagnosis, an irregular shape detection diagnosis, a hypercoiled cord identification diagnosis, or a knot detection diagnosis.

10. A system for providing a suggested pathological diagnosis of a placenta based on image data pertaining to the placenta, the system comprising:
    one or more processing devices; and
    one or more non-transitory, processor-readable storage mediums having programming instructions thereon that, when executed, cause the one or more processing devices to:
       receive the image data pertaining to the placenta from a morphological characterization system,
       extract a first segmentation map for a classified fetal side image of the placenta and a second segmentation map for a classified maternal side image of the placenta from the image data,
       determine, from the first segmentation map and the second segmentation map, pixels pertaining to a target portion to obtain a processed placenta photo,
       transmit the processed placenta photo to a neural network together with a set of instructions for determining one or more features of the target portion,
       receive an output from the neural network that comprises a determined pathological diagnosis from the one or more features of the target portion, and
       provide the determined pathological diagnosis to an external device as a suggested pathological diagnosis of the placenta.

11. The system of claim 10, wherein the suggested pathological diagnosis is a retained placenta classification diagnosis, a retained placenta localization diagnosis, an insertion type categorization diagnosis, a meconium detection diagnosis, an abruption detection diagnosis, a chorioamnionitis detection diagnosis, an irregular shape detection diagnosis, a hypercoiled cord identification diagnosis, or a knot detection diagnosis.

12. The system of claim 10, wherein the target portion is one or more of the placenta, a disc, a ruler placed adjacent to the placenta, and an umbilical cord.

13. The system of claim 10, wherein the neural network is a Resnet-18 network that is pretrained on ImageNet using mini-batched stochastic gradient descent with batch size 10, learning rate 0.01, momentum 0.9, and weight decay 0.0005.

14. The system of claim 10, wherein the neural network:
recovers an occluded disc area from the processed placenta photo by vertices adjacent with a disc area and a cord area;
extracts scale information from a ruler within the processed placenta photo;
binarizes a plurality of pixels within a region corresponding to the ruler to obtain a distinct scale marker;
uses kernel density estimation to fit a distribution of marker pixels from the distinct scale marker along a long edge of the ruler;
reads a number of pixels corresponding to one centimeter as a number of pixels between two adjacent crests of an estimated distribution;
estimates a long-axis and a short-axis of the placenta;
estimates a distance from an insertion point to a nearest point on a disc margin;
calculates a ratio of the distance from the insertion point to the nearest point on the disc margin to an average length of the long-axis and the short-axis; and
conducts a classification based on pre-selected thresholds based on optimizing training set classification accuracy.

15. The system of claim 10, wherein the neural network is a 6-layer convolutional neural network that is trained on a disc region of the placenta to detect one or more of meconium, abruption, and chorioamnionitis in the placenta.

16. The system of claim 10, wherein the neural network:
recovers an occluded disc area from the processed placenta photo by vertices adjacent with a disc area and a cord area to produce a whole disc region as a binary map;
finds a best-fit ellipse using zeroth-, first-order and second-order moments;
counts a number of pixels covered by the best-fit ellipse, a number of disc pixels outside the best-fit ellipse, and a number of non-disc pixels within the best-fit ellipse; and
use the number of pixels covered by the best-fit ellipse, the number of disc pixels outside the best-fit ellipse, and the number of non-disc pixels within the best-fit ellipse as a measure of irregularity for disc shape, wherein the neural network utilizes a training set to classify the measure of irregularity as being irregular when above a predetermined threshold.

17. The system of claim 10, wherein the neural network applies Canny edge detection to one or more portions of the processed placenta photo indicated as a cord region to detect fold crevices caused by hypercoiling.

18. The system of claim 10, wherein the neural network is a single edge detection network that uses the processes placenta photo concatenated with a binary mask indicating a cord region as an input trained against expert-labeled bounding boxes for knots.

* * * * *